United States Patent
Oue et al.

(10) Patent No.: US 11,927,516 B2
(45) Date of Patent: Mar. 12, 2024

(54) SAMPLE SCRAPING METHOD AND SAMPLE SCRAPING DEVICE

(71) Applicant: SYSMEX CORPORATION, Kobe (JP)

(72) Inventors: Soichi Oue, Kobe (JP); Yutaka Maeda, Kobe (JP); Junyi Ding, Kobe (JP); Takayuki Koshihara, Kobe (JP); Hironori Kobayashi, Kobe (JP); Yasuhiro Kouchi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 174 days.

(21) Appl. No.: 17/671,634

(22) Filed: Feb. 15, 2022

(65) Prior Publication Data

US 2022/0260465 A1 Aug. 18, 2022

(30) Foreign Application Priority Data

Feb. 17, 2021 (JP) .................. 2021-023716

(51) Int. Cl.
*G01N 1/06* (2006.01)
*G01N 1/44* (2006.01)
*G01N 33/483* (2006.01)

(52) U.S. Cl.
CPC ......... *G01N 1/44* (2013.01); *G01N 2001/061* (2013.01); *G01N 33/4833* (2013.01)

(58) Field of Classification Search
CPC .............. G01N 1/44; G01N 33/4833; G01N 2001/061; G01N 1/286; G01N 1/00; G01N 1/2806; G01N 2001/2873; G01N 1/36

USPC ...... 73/863, 863.01, 863.11, 864.41; 83/919; 600/300–595
See application file for complete search history.

(56) References Cited

U.S. PATENT DOCUMENTS

| | | | |
|---|---|---|---|
| 11,332,777 B1 * | 5/2022 | Xu | B01L 7/525 |
| 2016/0131559 A1 | 5/2016 | Wimberger-Friedl et al. | |
| 2018/0128714 A1 | 5/2018 | Adey et al. | |
| 2019/0390252 A1 * | 12/2019 | Yeung | C12Q 1/6813 |

FOREIGN PATENT DOCUMENTS

| | | | |
|---|---|---|---|
| CN | 210376349 U | * | 4/2020 |
| JP | 6535657 B2 | | 6/2019 |
| JP | 2020-502540 A | | 1/2020 |
| WO | WO-2019246376 A1 | * | 12/2019 |

OTHER PUBLICATIONS

Sysmex Corporation, OncoGuide NCC OncoPanel System, p. 11-12.
Roche Sequencing Solutions, Avenio Millisect System—Software version 2.0.0—User Guide—Version 4.0, pp. 1-136.

* cited by examiner

*Primary Examiner* — Robert R Raevis
(74) *Attorney, Agent, or Firm* — METROLEX IP LAW GROUP, PLLC

(57) ABSTRACT

A sample scraping method and a sample scraping device capable of efficiently scraping and collecting a biological tissue section without waste while suppressing contamination is provided. In a sample scraping method for scraping and collecting a biological tissue section held on a slide, the FFPE section held on the slide is heated, and the heated FFPE section is scraped by a blade such that the FFPE section that has been scraped off and remains on the blade is collected in a container.

26 Claims, 19 Drawing Sheets

First modification

Third modification

FIG. 16A  Second embodiment

FIG. 19A  Third embodiment
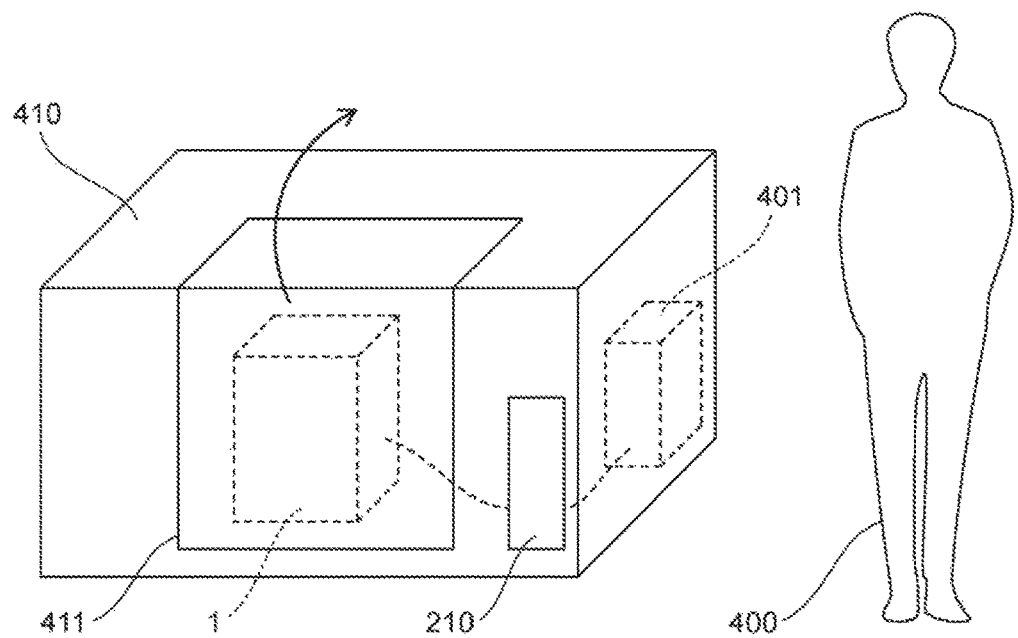
FIG. 19B
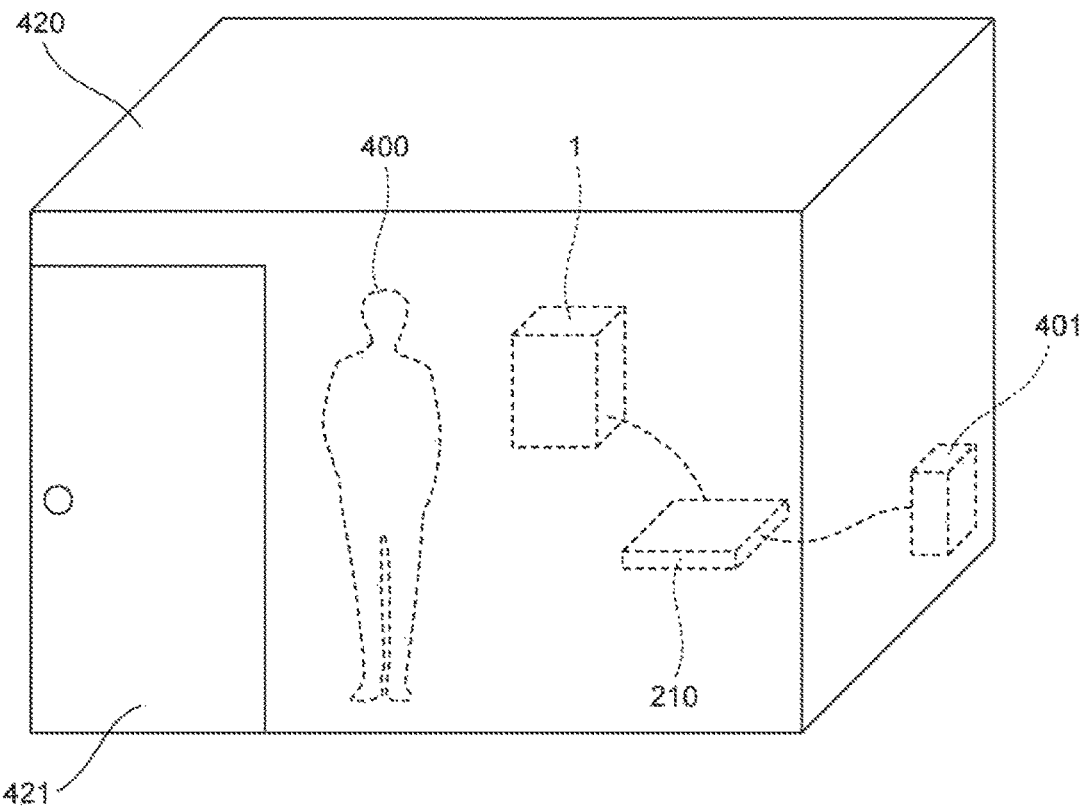

SAMPLE SCRAPING METHOD AND SAMPLE SCRAPING DEVICE

CROSS REFERENCE TO RELATED APPLICATIONS

This application claims priority from prior Japanese Patent Application(s) No. 2021-023716, filed on Feb. 17, 2021, entitled "SAMPLE SCRAPING METHOD AND SAMPLE SCRAPING DEVICE", the entire contents of which are incorporated herein by reference.

FIELD OF THE INVENTION

The present invention relates to a sample scraping method and a sample scraping device for scraping and collecting a part or all of a biological tissue section on a slide.

BACKGROUND

In a genetic panel test, it is necessary to manually scrape the FFPE section from the slide holding the formalin-fixed paraffin-embedded tissue section (FFPE section) using a razor and collect the scraped FFPE section in a container. The following Japanese Patent Publication No. 2020-502540 describes an apparatus in which the tissue in the region of interest is scraped from the slide on which the FFPE section is held by the rotational operation of a cutting blade, the tissue is crushed, and then the tissue is suctioned to a chip and collected in a container.

SUMMARY OF THE INVENTION

When manually scraping and recovering a biological section held on a slide using a razor, it is difficult to efficiently scrape and recover the FFPE section without waste, and the scraped FFPE section is scattered and other contamination can be caused by entering a container for collecting FFPE sections. Even if an apparatus such as described in Japanese Patent Publication No. 2020-502540 is used, there is a problem that the cost and time for collecting the FFPE section held on the slide will increase because a complicated process is required to collect the FFPE section.

In view of these problems, the present invention provides a sample scraping method and a sample scraping device capable of efficiently scraping and recovering a biological tissue section while suppressing contamination.

In the sample scraping method according to the present invention, a biological tissue section (121) held on a slide (120) is heated (S13, S101), and the heated biological tissue section (121) is scraped off by the blade (110) (S14, S102), then the biological tissue section (121) remaining on the blade (110) is collected in the container (140) (S15, S16, S31, S32, S106 to S109).

According to the sample scraping method according to the present invention, since the biological tissue section is heated and softened when the biological tissue section is scraped off, the biological tissue section can be scraped off stably and smoothly. Hence, the biological tissue section can be efficiently scraped and recovered without waste. Since the softened biological tissue section is scraped off by the blade, the scraped biological tissue section tends to adhere to the blade and remain thereon. Therefore, it is possible to suppress the scattering of the biological tissue section remaining on the blade, and it is possible to suppress contamination due to such scattering.

The sample scraping device (1) according to the present invention comprises a slide installation unit (51) on which a slide (120) holding a biological tissue section (121) is installed, a heating unit (61) for heating the biological tissue section (121) on a slide (120) installed on the slide installation unit (51), and a moving mechanism (230) for scraping off the biological tissue section (121) with a blade (110).

According to the sample scraping device according to the present invention, the same effect as the sample scraping method according to the present invention can be obtained. The burden on the user also can be reduced and the biological tissue section can be collected.

According to the present invention, a biological tissue section can be efficiently scraped off and recovered while suppressing contamination.

BRIEF DESCRIPTION OF THE DRAWINGS

FIG. 16A is a front view schematically showing a structure of a sample scraping device according to a second embodiment.

FIG. 19A is a perspective view schematically showing a structure according to a third embodiment; and FIG. 19B is a perspective view schematically showing a structure according to a modified example of the third embodiment.

DESCRIPTION OF THE EMBODIMENTS OF THE INVENTION

Figure 1:
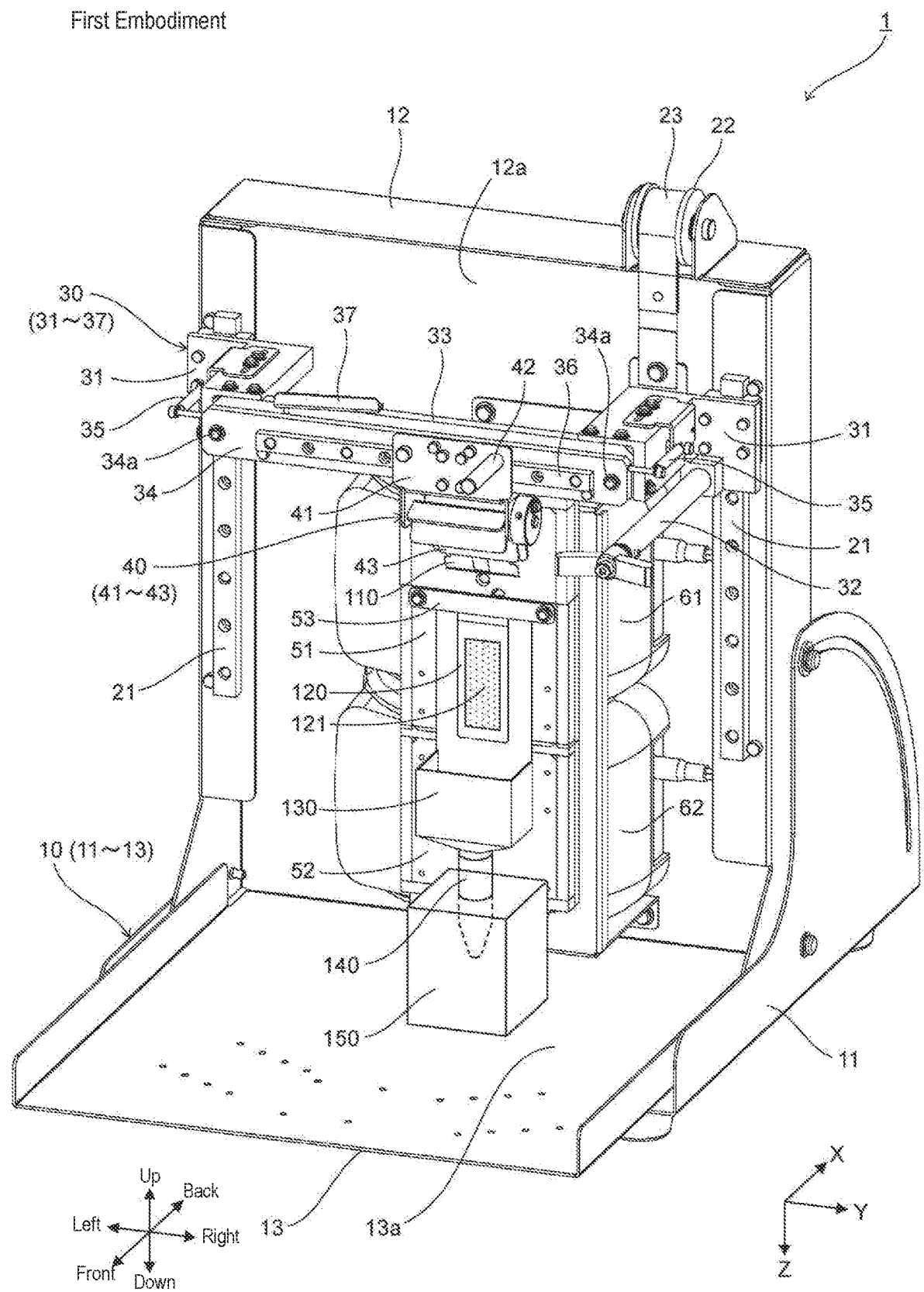
FIG. 1 is a perspective view showing the structure of a sample scraping device according to the first embodiment.

The following embodiments show a sample scraping method and a sample scraping device for scraping and collecting a part of a biological tissue section held on a slide. In the following embodiments, the biological tissue section is a section (hereinafter referred to as "FFPE section") of a formalin-fixed paraffin-embedded tissue (FFPE tissue).

In the following description and drawings, the same reference numerals will indicate the same or similar components, and description of the same or similar components will be omitted. For convenience, the X, Y, and Z axes that are orthogonal to each other are appropriately added to each figure, and the X, Y, and Z axes correspond to the front-back direction, the left-right direction, and the up-down direction, respectively.

First Embodiment

In the first embodiment, the user manually operates the moving mechanism of the sample scraping device 1 to scrap and collect the FFPE section.

Figure 2:
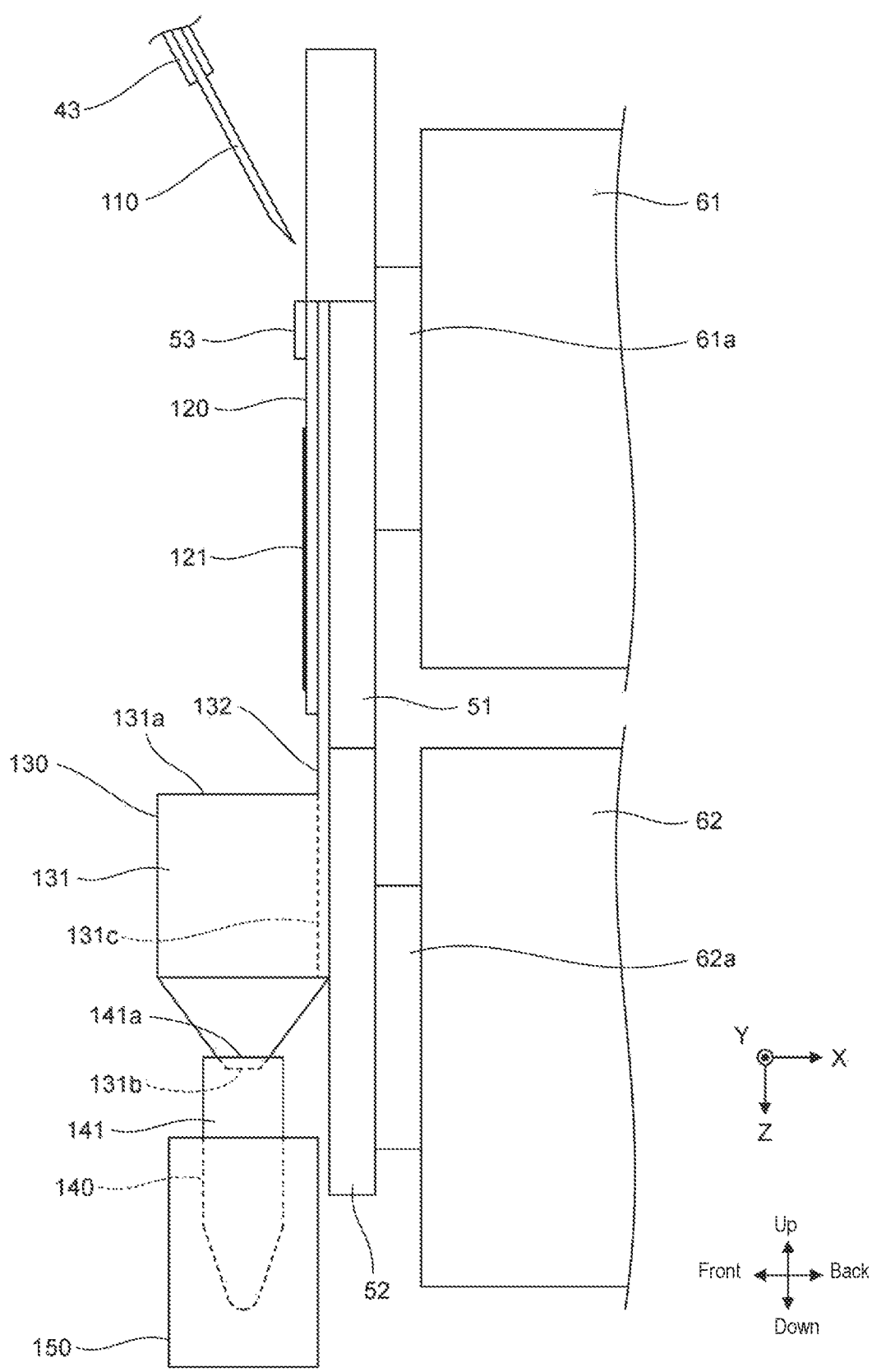
FIG. 2 is a side view schematically showing the structure in the vicinity of a slide installation unit and a guide portion installation unit according to the first embodiment.

FIG. 1 is a perspective view showing the structure of the sample scraping device 1. FIG. 2 is a side view schematically showing a structure in the vicinity of the slide installation unit 51 and the guide portion installation unit 52.

As shown in FIG. 1, the sample scraping device 1 includes a housing 10, a pair of guide rails 21, a pulley 22, a belt 23, a vertical moving unit 30, a left-right moving unit 40, and a slide installation unit 51, a guide portion installation unit 52, a fastener 53, a heating unit 61, and a cooling unit 62. The guide rail 21, the pulley 22, the belt 23, the vertical moving unit 30, and the left-right moving unit 40 form a moving mechanism that moves the blade 110 relative to the slide 120.

The housing 10 (11 to 13) includes a base member 11, a wall member 12, and a container mounting member 13. The wall member 12 is supported by the base member 11. The wall member 12 includes a flat plate 12a. The container mounting member 13 is provided with a flat plate 13a on the XY plane (horizontal plane). The wall member 12 and the container mounting member 13 are arranged so that the flat plate 12a is perpendicular to the flat plate 13a. A container rack 150 for holding a container 140, which will be described later, is placed on the upper surface of the flat plate 13a of the container mounting member 13.

A pair of guide rails 21 parallel to each other are installed so as to extend in the vertical direction at the right end and the left end on the front surface side of the wall member 12, respectively. The pulley 22 is installed at the upper end of the wall member 12, and the belt 23 is wound around the pulley 22. The belt 23 is made of metal.

The vertical movement unit 30 (31 to 37) includes a pair of vertical movement members 31, a vertical movement lever 32, a plate member 33, a front-rear movement member 34, a pair of springs 35, a guide rail 36, and a switching lever 37. The pair of vertically moving members 31 are installed on the left and right guide rails 21 so as to be movable in the vertical direction along the guide rails 21. One end of the belt 23 is installed on the vertical movement member 31 on the right side. The vertical movement lever 32 is a rod-shaped member extending forward, and is installed on the vertical movement member 31 on the right side.

The plate member 33 is installed on the pair of vertically moving members 31 so as to straddle the pair of vertically moving members 31. Pins 34a extending in the front-rear direction are installed at the left and right ends of the front-back moving member 34, respectively. By passing the pins 34a through the holes provided at the left and right ends of the plate member 33, the front-rear moving member 34 is supported so as to be movable in the front-rear direction with respect to the plate member 33. The spring 35 on the right side connects the right end of the front-back moving member 34 and the up-down moving member 31 on the right side, and the spring 35 on the left side connects the left end of the front-back moving member 34 and the up-down moving member 31 on the left side. The guide rail 36 is installed so as to extend in the left-right direction on the front surface of the front-rear moving member 34. The switching lever 37 is installed on the plate member 33, and defines the distance between the plate member 33 and the front-back moving member 34.

The left-right moving unit 40 (41 to 43) includes a left-right moving member 41, a left-right moving lever 42, and a blade installing unit 43. The left-right moving member 41 is installed on the guide rail 36 so as to be movable in the left-right direction along the guide rail 36. The left-right moving lever 42 is a rod-shaped member extending forward, and is installed on the left-right moving member 41. The blade installation unit 43 is installed below the left-right moving member 41, and is configured to be able to hold the blade 110. The blade 110 is used to scrape off the FFPE section 121 held on the slide 120, and is replaced every time the slide 120 changes. As the blade 110, for example, Art Knife Pro spare blade flat sword XB157H (manufactured by Olfa Co., Ltd.), razor spare blade carbon steel (manufactured by Feather Safety Razor Co., Ltd.) and the like can be used.

When the user moves the vertical movement lever 32 in the vertical direction, the vertical movement unit 30, the left-right movement unit 40, and the blade 110 move up and down along the guide rail 21. The vertical movement member 31 on the right side is connected to the pulley 22 via a metal belt 23, and the metal belt 23 has rigidity and does not deform due to the downward force exerted due to the weight of the vertical movement unit 30, the left-right movement unit 40, and the blade 110. Therefore, even if the user manually releases the vertical movement lever 32, the vertical movement unit 30, the left-right movement unit 40, and the blade 110 stop at that position. When the user moves the left-right movement lever 42 in the left-right direction, the left-right movement unit 40 and the blade 110 move left and right along the guide rail 36.

When the user operates the switching lever 37, the front-back moving member 34 is switched between being separated from the plate member 33 by a predetermined distance against the exerted force of the spring 35, and being in contact with the plate member 33 in accordance with the force exerted by the spring 35. In this way, the blade 110 can be switched between a state in which the blade 110 is separated forward with respect to the slide 120 and a state in which the blade 110 is pressed backward with respect to the slide 120.

The slide installation unit 51 and the guide portion installation unit 52 are plate-shaped members made of a material having high thermal conductivity. The slide installation unit 51 and the guide portion installation unit 52 are made of a metal material such as aluminum. The front surface of the slide installation unit 51 and the guide portion installation unit 52 is a flat surface, and is installed relative to the wall member 12 so as to be parallel to the flat plate 12a of the wall member 12. In this way the front surface of the slide installation unit 51 and the guide portion installation unit 52 becomes perpendicular to the horizontal plane.

Slide 120 is an FFPE specimen slide. The slide 120 is a plate-shaped member made of a transparent material such as glass. The slide 120 holds the FFPE section 121 in advance. It is preferable that the FFPE section 121 is prepared in accordance with the "Rules for Handling Pathological Tissue Specimens for Genome Medical Treatment" formulated by the Japanese Pathological Society. The guide portion 130 has a funnel shape and is made of resin. The guide portion 130 is replaced every time the slide 120 changes.

The fastener 53 is a plate-shaped member extending in the left-right direction, and screw holes are provided at the left and right ends of the fastener 53. With the slide 120 and the guide portion 130 sandwiched between the fastener 53 and the slide installation unit 51, the screw is fastened to the slide installation unit 51 through the screw hole of the fastener 53. In this way the slide 120 is installed in the slide installation portion 51, and the guide portion 130 is installed in the guide portion installation portion 52.

As shown in FIG. 2, the heating unit 61 heats the slide installation unit 51 from the rear side, and the cooling unit 62 cools the guide unit installation unit 52 from the rear side. The heating unit 61 and the cooling unit 62 have the same structure. The heating unit 61 includes a Peltier element, a heat sink connected to the Peltier element, and a heat conductive member 61a. The cooling unit 62 includes a Peltier element, a heat sink connected to the Peltier element, and a heat conductive member 62a. By reversing the polarities of the currents flowing through the respective Peltier elements of the heating unit 61 and the cooling unit 62, one becomes the heating unit 61 and the other becomes the cooling unit 62.

The container 140 is a container having an opening 141a at the upper end of the body portion 141, and is a container for collecting the scraped portion of the FFPE section 121. In the following, the FFPE section 121 remaining on the blade 110 is referred to as a scraped portion. The container 140 is preferably a container such as a resin Eppendorf tube that can be used in the nucleic acid extraction step performed after the treatment of the sample scraping device 1. The container rack 150 is a box-shaped rack that can hold the container 140 in an upright position. The container rack 150 is placed on the upper surface of the flat plate 13a of the container mounting member 13 of the housing 10 so that the container 140 is positioned below the guide portion 130.

The guide portion 130 includes a body 131 and a connection surface 132. The body 131 has a tubular shape penetrating in the vertical direction. In the left-right direction (Y-axis direction), the left-right length (width) of the upper opening 131a located at the upper end of the body 131 is the left-right length (width) of the FFPE section 121 held on the slide 120. The lower opening 131b located at the lower end of the body 131 is smaller than the upper opening 131a of the body 131. The lower opening 131b of the guide portion 130 is smaller than the opening 141a at the upper end of the container 140. The connecting surface 132 extends upward from the rear side of the body 131 and has a surface shape parallel to the YZ plane.

The connection surface 132 and the slide 120 are installed at the upper end of the slide installation unit 51 by the fastener 53 so that the connection surface 132 is located behind the slide 120. At this time, the slide 120 is positioned above the upper opening 131a of the guide portion 130. The slide 120 is in close contact with the slide installation unit 51 via the connection surface 132, and the rear portion of the body 131 of the guide portion 130 is in close contact with the guide portion installation unit 52.

The heat conductive member 61a of the heating unit 61 is in close contact with the surface on the rear side of the slide installation unit 51, and the heating unit 61 heats the slide installation unit 51 via the heat conduction member 61a. In this way the slide 120 installed on the slide installation unit 51 is heated via the connection surface 132 of the guide portion 130, and the FFPE section 121 held on the slide 120 is heated. The heat conductive member 62a of the cooling unit 62 is in close contact with the surface on the rear side of the induction unit installation unit 52, and the cooling unit 62 cools the induction unit installation unit 52 via the heat conduction member 62a. In this way the rear inner side surface 131c (rear portion of the inner side surface of the body 131) of the body 131 installed in the guide portion installation unit 52 is cooled.

Next, heating, scraping, cooling, and recovery of the FFPE section 121 will be described with reference to FIGS. 3A to 5B.

FIGS. 3A and 3B and FIGS. 5A and 5B are side views schematically showing the structure in the vicinity of the slide installation unit 51 and the guide portion installation unit 52. FIG. 4A is an enlarged view schematically showing the structure of the tip of the blade 110. FIG. 4B is a front view schematically showing the structure in the vicinity of the slide installation unit 51 and the guide portion installation unit 52.

Figure 3A:
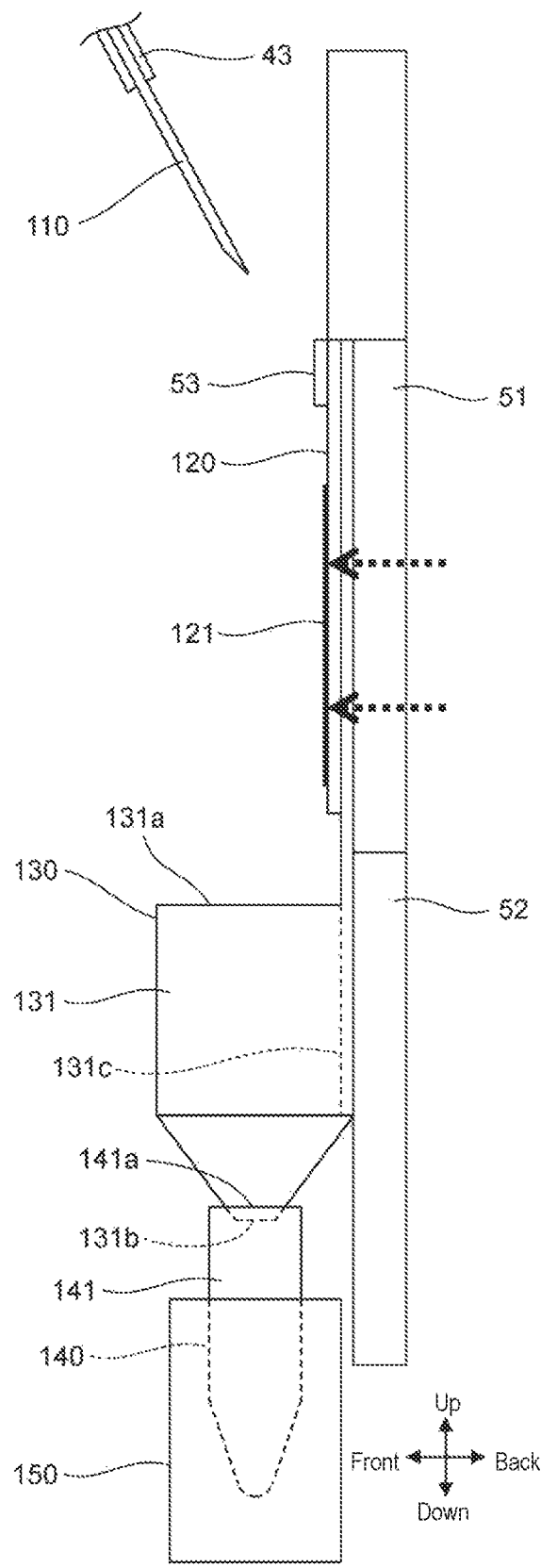
FIGS. 3A and 3B are side views respectively schematically showing the structures in the vicinity of a slide installation unit and a guide portion installation unit according to the first embodiment.
Figure 4A:
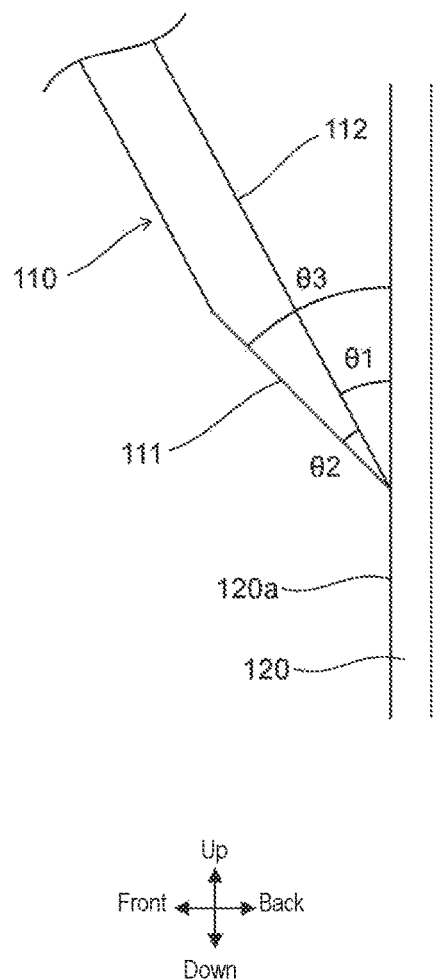
FIG. 4A is an enlarged view schematically showing the structure of a tip of a blade according to the first embodiment.
Figure 4B:
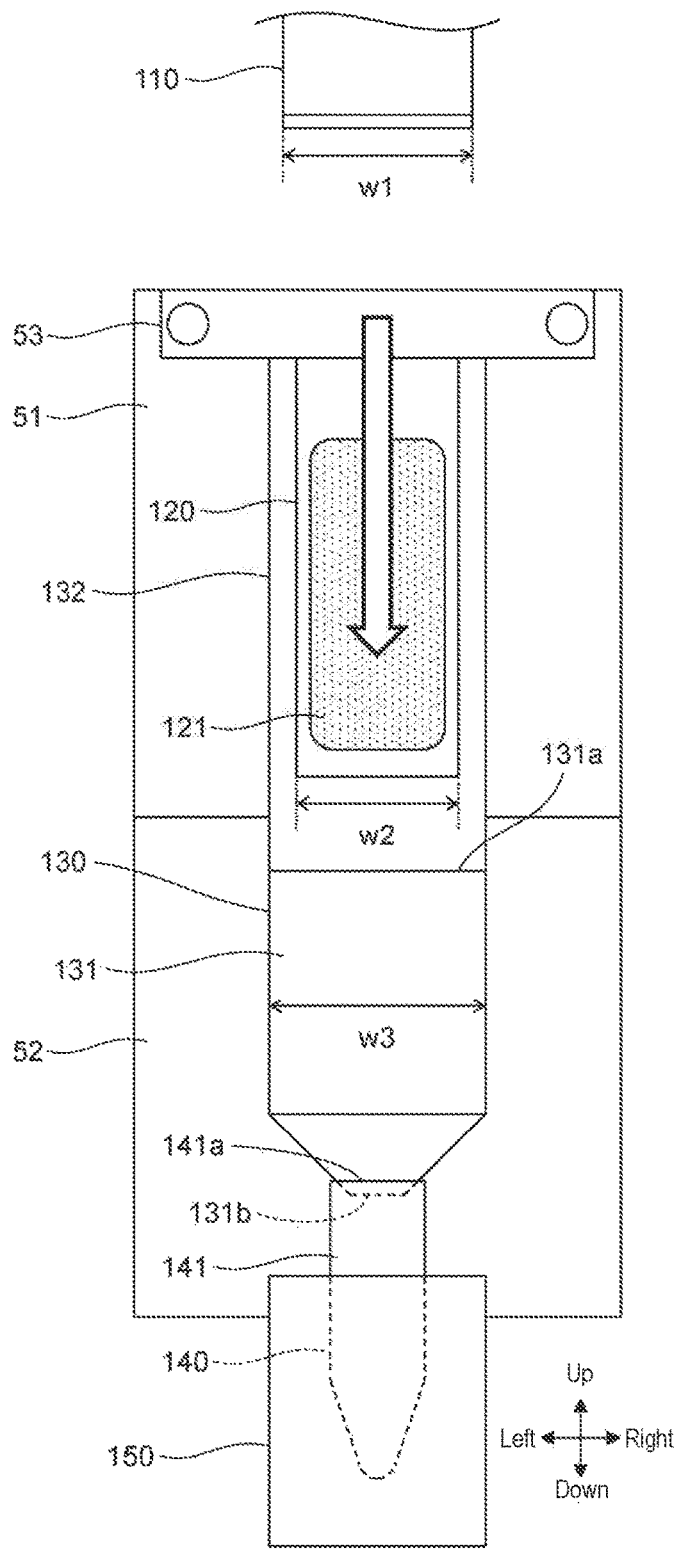
FIG. 4B is a front view schematically showing the structure of the vicinity of the slide installation unit and the guide portion installation unit according to the first embodiment.

As shown in FIG. 3A, when scraping and collecting the FFPE section 121 from the slide 120, the user first moves the vertical movement lever 32 (see FIG. 1) to the uppermost position, and then operates the switching lever 37 (see FIG. 1) so that the blade 110 is separated forward from the slide installation unit 51. Then, the user installs the slide 120 to be scraped and the new guide portion 130 in the slide installation unit 51 by using the fastener 53. The user installs the new blade 110 in the blade installation unit 43, and positions the opening 141a of the new container 140 in the lower opening 131b of the guide portion 130.

Subsequently, the user heats the FFPE section 121 held on the slide 120 by activating the heating unit 61 and heating the slide installation unit 51. According to a study by the inventors, by setting the heating temperature of the FFPE section 121 to 40° C. to 50° C., the FFPE section 121 on the slide 120 does not become completely liquid, and the section 121 can be softened to such an extent that it can be smoothly scraped off by the blade 110.

Figure 3B:
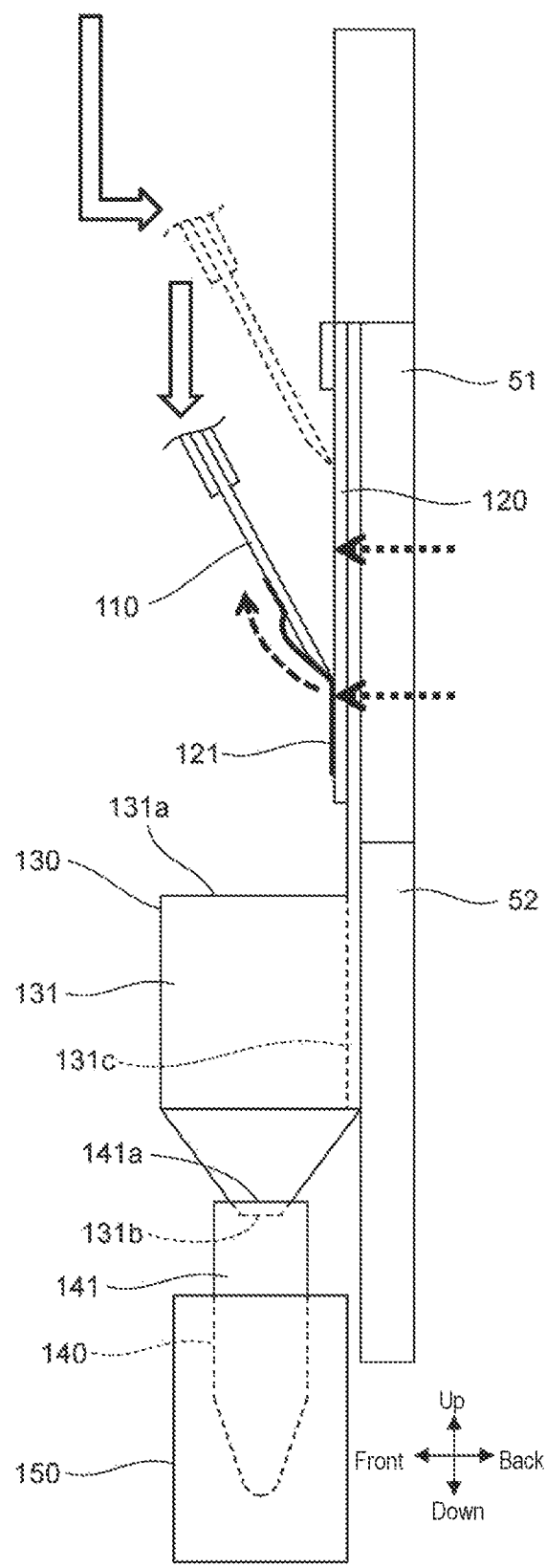

Subsequently, as shown in FIG. 3B, the user moves the vertical movement lever 32 and the left-right movement lever 42 so that the tip of the blade 110 is positioned in front of the slide 120, and operates the switching lever 37 so that the blade 110 is urged rearward as shown by the dashed line such that the tip of the blade 110 is positioned on the surface of the slide 120. From this state, the user moves the vertical movement lever 32 downward and moves the tip of the blade 110 downward along the surface of the slide 120. In this way the FFPE section 121 held on the slide 120 is scraped off, and the scraped portion of the FFPE section 121 is held on the blade surface 111 of the blade 110 (see FIG. 4A).

As shown in FIG. 4A, the blade surface 111 is a surface on the front side of the blade 110, that is, a rake surface. The back surface 112 is a surface on the rear side of the blade 110, that is, a flank surface. The angle θ3 between the blade surface 111 and the slide surface 120a of the slide 120 is the sum of the angle θ1 between the back surface 112 and the slide surface 120a and the angle θ2 (blade angle) at the tip of the blade 110. According to the study by the inventors, when the angle θ3 is set to 38° to 51°, the scraped portion of the FFPE section 121 scraped by the blade 110 tends to remain on the blade 110 (blade surface 111). In this way the scraped portion can be efficiently recovered.

As shown in FIG. 4B, in the first embodiment, the width w1 of the blade 110 is larger than the width w2 of the slide 120 in the left-right direction. Therefore, in a state in which the center position of the blade 110 is aligned with the center position of the slide 120 in the left-right direction, the blade 110 scrapes the FFPE section 121 on the slide 120, whereby the FFPE section 121 on the slide 120 can be scraped off in one scraping step as the blade 110 scrapes on the slide 120 in one scraping operation. In the left-right direction, the width w3 of the upper opening 131a is larger than the width in the left-right direction of the FFPE section 121 held on the slide 120, and also is larger than the width w2 of the slide 120. In this way all the FFPE sections 121 scraped off by the blade 110 are guided to the guide portion 130.

Figure 5A:
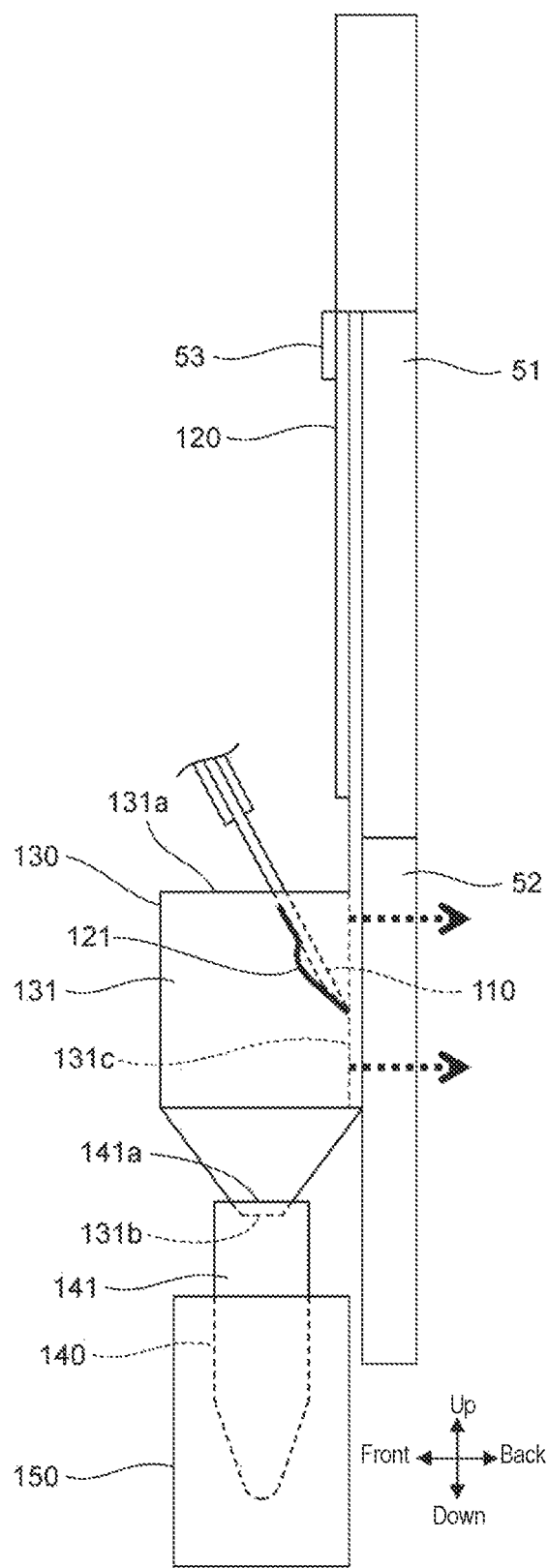
FIGS. 5A and 5B are side views schematically showing the structures in the vicinity of a slide installation unit and a guide portion installation unit according to the first embodiment, respectively.

As shown in FIG. 5A, when the scraping of the FFPE section 121 is completed, the user moves the vertical movement lever 32 so that the tip of the blade 110 is positioned on the rear inner side surface 131c of the guide portion 130. Then, the user activates the cooling unit 62 to cool the guide unit installation unit 52, thereby cooling the scraped portion of the FFPE section 121 held by the blade 110. According to the study by the inventors, by setting the cooling temperature of the scraped portion to 5° C. to 20° C., the scraped portion of the FFPE section 121 on the blade 110 can be solidified, and condensation on the scraped portion can be suppressed.

Figure 5B:
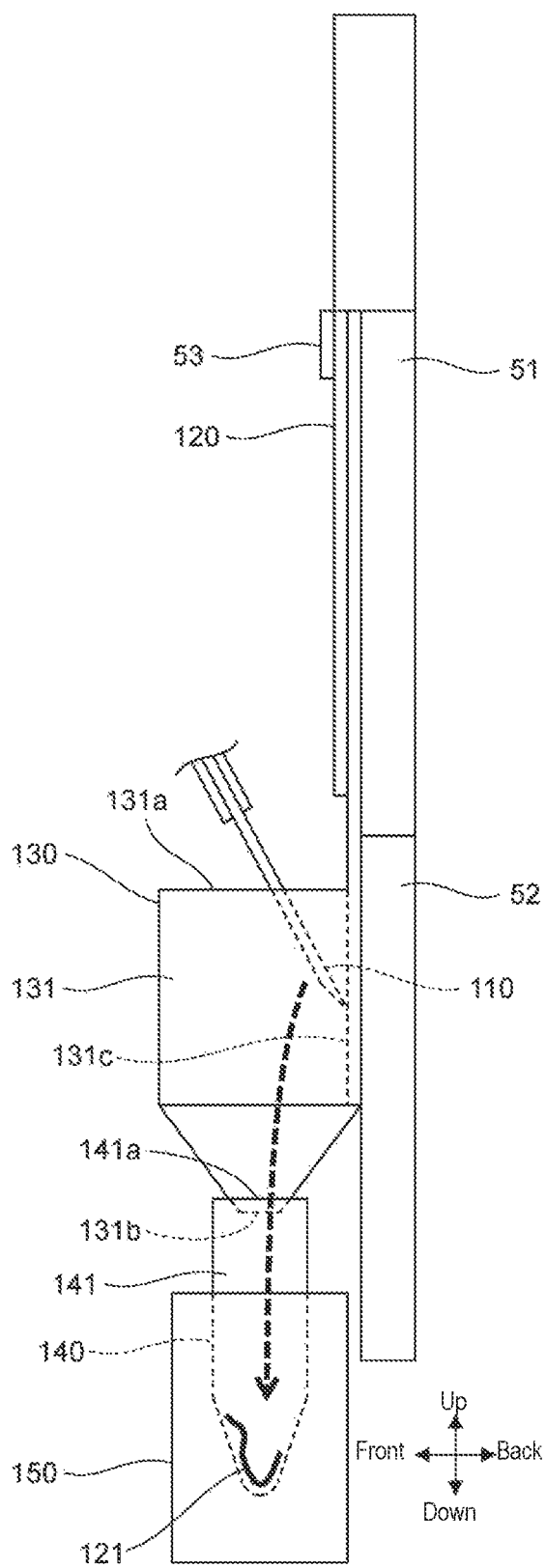

As shown in FIG. 5B, when time elapses from the state of FIG. 5A, the solidified FFPE section 121 falls from the blade 110 due to gravity. The scraped portion of the dropped FFPE section 121 is guided by the guide portion 130, passes through the opening 141a of the container 140, and is collected in the container 140. In this way, the recovery of the FFPE section 121 is completed.

Figure 6:
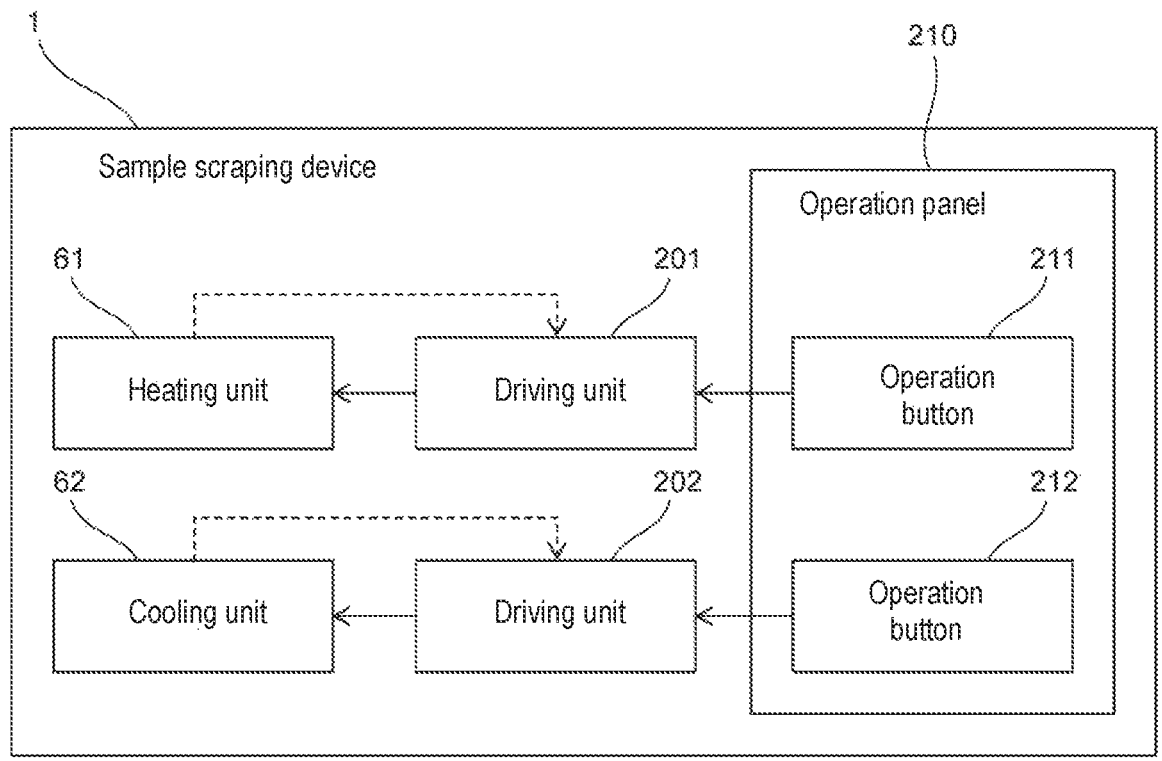
FIG. 6 is a block diagram showing a structure of a sample scraping device according to the first embodiment.

FIG. 6 is a block diagram showing the structure of the sample scraping device 1.

The sample scraping device 1 includes a heating unit 61, a cooling unit 62, driving units 201 and 202, and an operation panel 210.

The operation panel 210 includes operation buttons 211 and 212. When the user operates the operation button 211, the drive unit 201 drives the heating unit 61 in response to the operation. The drive unit 201 controls the heating unit 61 so that the heating temperature by the heating unit 61 becomes a predetermined temperature in response to the feedback from the heating unit 61. When the user operates the operation button 212, the drive unit 202 drives the cooling unit 62 in response to the operation. The drive unit 202 controls the cooling unit 62 so that the cooling temperature by the cooling unit 62 becomes a predetermined temperature in response to the feedback from the cooling unit 62.

Figure 7:
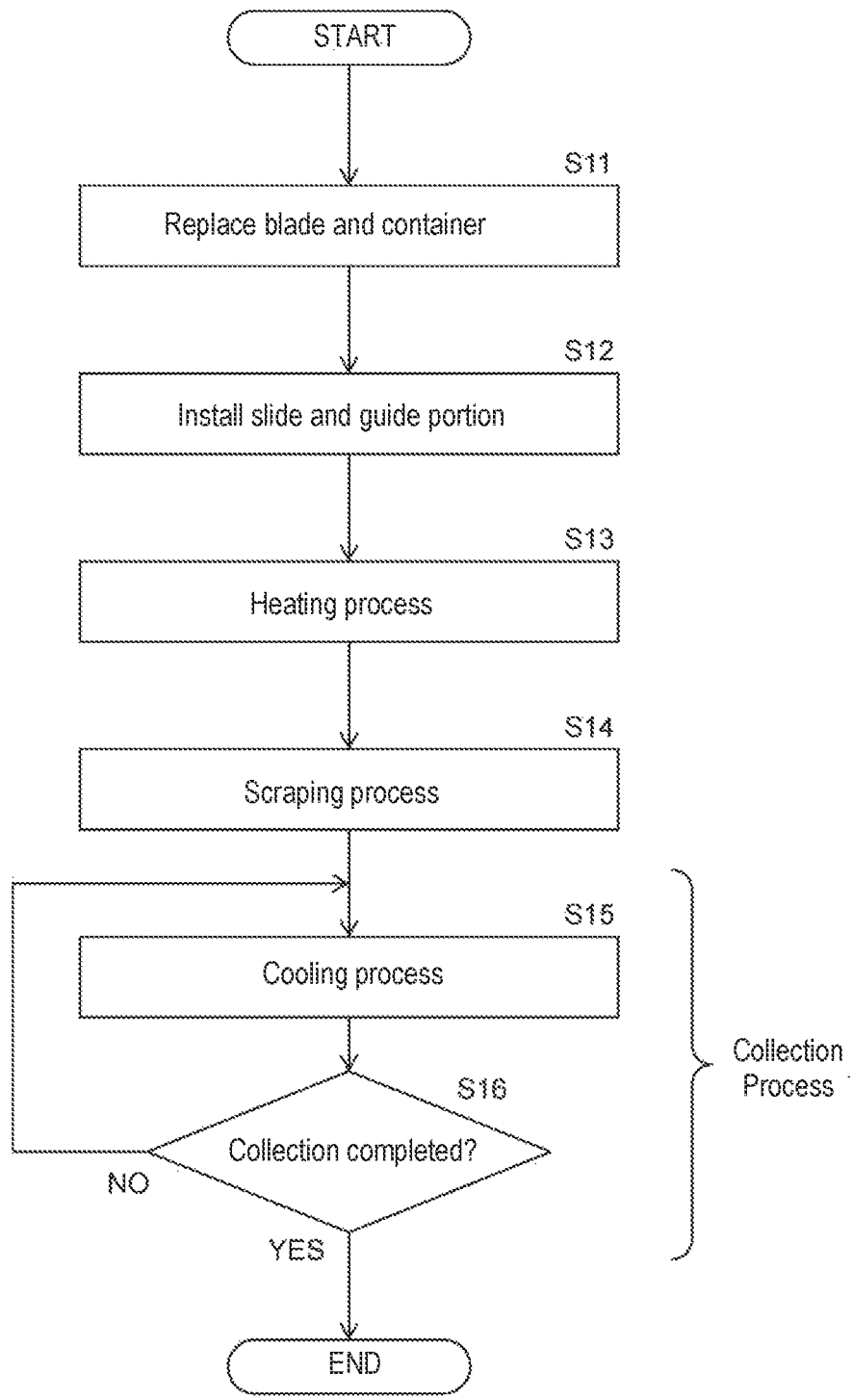
FIG. 7 is a flowchart showing a sample scraping method using a sample scraping device according to the first embodiment.

FIG. 7 is a flowchart showing a sample scraping method using the sample scraping device 1.

In step S11, the user replaces the blade 110 and the container 140 with new blade 110 and container 140 as shown in FIG. 3A. In step S12, as shown in FIG. 3A, the user installs the slide 120 to be scraped and the new guide portion 130 on the slide installation unit 51 using the fastener 53.

In the heating process of step S13, the user operates the operation button 211 (see FIG. 6) to drive the heating unit 61 to heat the FFPE section 121 held on the slide 120. In the scraping process of step S14, as shown in FIG. 3B, the user uses the blade 110 to scrape the FFPE section 121 held on the slide 120 so as to be held on the blade surface 111 (see FIG. 4A).

Subsequently, the user executes the collection process. The collection step is composed of a cooling step in step S15 and a determination in step S16.

In the cooling process of step S15, the user positions the tip of the blade 110 on the rear inner side surface 131c as shown in FIG. 5A. In step S15, the user operates the operation button 212 (see FIG. 6) to drive the cooling unit 62 to cool the scraped portion of the FFPE section 121 on the blade 110. In step S16, as shown in FIG. 5B, the user visually determines whether the scraped portion of the FFPE section 121 on the blade 110 has been collected in the container 140.

If the scraped portion of the FFPE section 121 has not been recovered (step S16: NO), the user returns the process to step S15 and continues cooling the scraped portion of the FFPE section 121 on the blade 110. However, when the scraped portion of the FFPE section 121 is recovered (step S16: YES), the process of FIG. 7 is completed.

Effect of the First Embodiment

According to the first embodiment, the following effects are achieved.

In the heating process of step S13, the FFPE section 121 held on the slide 120 is heated. In the scraping process of step S14, the blade 110 is moved relative to the slide 120, and the heated FFPE section 121 is scraped. In the collection step of FIG. 7, the scraped portion of the FFPE section 121 remaining on the blade 110 is collected in the container 140.

According to this structure, when the FFPE section 121 is scraped, the FFPE section 121 is heated and softened, so that the FFPE section 121 can be scraped stably and smoothly. Hence, the FFPE section 121 can be efficiently scraped and recovered without waste. Since the softened FFPE section 121 is scraped by the blade 110, the scraped FFPE section 121 tends to adhere to the blade 110 and remain thereon. Therefore, it is possible to suppress the scattering of the biological tissue section remaining on the blade 110, and it is possible to suppress contamination due to such scattering.

In the cooling process of step S15, the scraped portion of the FFPE section 121 remaining on the blade 110 is cooled by the cooling unit 62. In this way the scraped portion of the FFPE section 121 is solidified and easily peeled from the blade 110, so that the scraped portion can be smoothly collected in the container 140.

In the cooling process of step S15, the blade 110 is thermally coupled to the rear inner side surface 131c (cooling surface) of the guide portion 130, and the scraped portion of the FFPE section 121 is cooled by the cooling unit 62. In this way the scraped portion of the FFPE section 121 can be smoothly cooled.

The cooling temperature of the scraped portion of the FFPE section 121 is 5° C. to 20° C. In this way the scraped portion can be solidified, and it is possible to prevent condensation from occurring on the scraped portion.

In the scraping process of step S14, the blade 110 is elastically pressed against the FFPE section 121 by the spring 35 (the force-exerting unit) shown in FIG. 1. In this way, as shown in FIG. 3B, when the blade 110 and the FFPE section 121 move relative to each other, the blade 110 continues to be pressed against the FFPE section 121. Therefore, the thin FFPE section 121 on the slide 120 can be smoothly scraped off.

In the scraping process of step S14, as shown in FIG. 4A, the angle θ3 between the blade surface 111 of the blade 110 and the slide surface 120a is 38° to 51°. In this way the scraped portion of the FFPE section 121 tends to remain on the blade 110 (blade surface 111), and the scraped portion can be efficiently collected.

The heating process of step S13 includes a step of heating the slide installation unit 51 (installation member) on which the slide 120 is installed. In the heating step, the slide 120 is thermally coupled to the connecting surface 132 (heating surface) of the guide portion 130, and the slide 120 is heated by the heating unit 61 via the connecting surface 132. In this way the FFPE section 121 held on the slide 120 can be smoothly heated.

The heating temperature of the FFPE section 121 is 40° C. to 50° C. When the heating temperature is set in this way, the FFPE section 121 on the slide 120 does not become completely liquid, and the FFPE section 121 on the slide 120 is sufficiently softened to be smoothly scraped off by the blade 110.

In the collection step of FIG. 7, the scraped portion of the FFPE section 121 dropped from the blade 110 is guided to the container 140 by the guide portion 130. In this way the scraped portion of the FFPE section 121 can be smoothly guided to the container 140.

The guide portion 130 has a funnel shape. As shown in FIG. 4B, the width of the upper opening 131a of the guide portion 130 is larger than the width of the FFPE section 121 held on the slide 120. In this way the FFPE section 121 scraped from the slide 120 can be guided into the guide portion 130 without omission. The lower opening 131b of the guide portion 130 is smaller than the opening 141a of the container 140. In this way all the FFPE sections 121 guided into the guide portion 130 can be guided into the container 140.

In step S11, the blade 110 is replaced each time the slide 120 (FFPE section 121) changes. In this way it is possible to prevent contamination of the FFPE section 121 via the blade 110. In step S12, the guide portion 130 is also replaced every time the slide 120 (FFPE section 121) changes. In this way even if the blade 110 comes into contact with the rear inner side surface 131c during cooling as described above, contamination of the FFPE section 121 via the guide portion 130 can be prevented.

First Modification

Figure 8A:
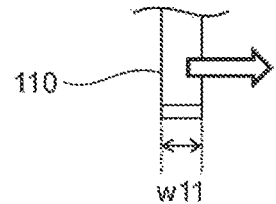
FIGS. 8A and 8B are front views schematically showing the structures of the vicinity of the slide installation unit and the guide portion installation unit according to the first modification, respectively.
Figure 8A:
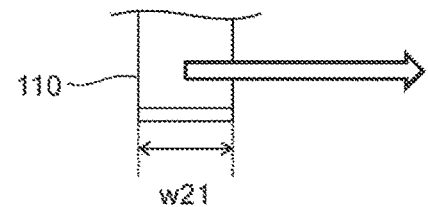
Figure 8A:
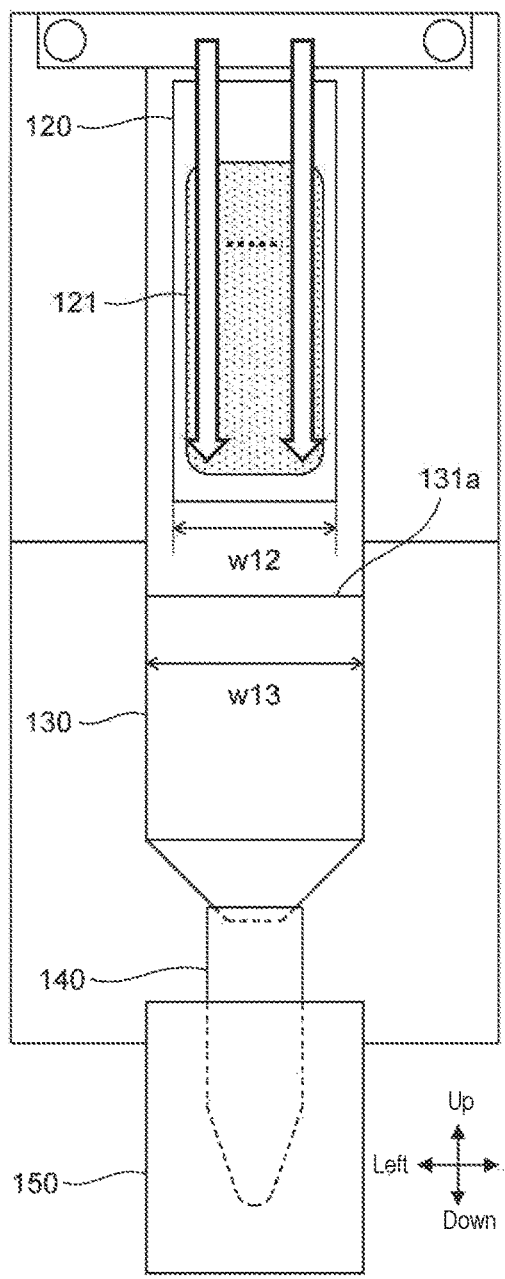
Figure 8B:
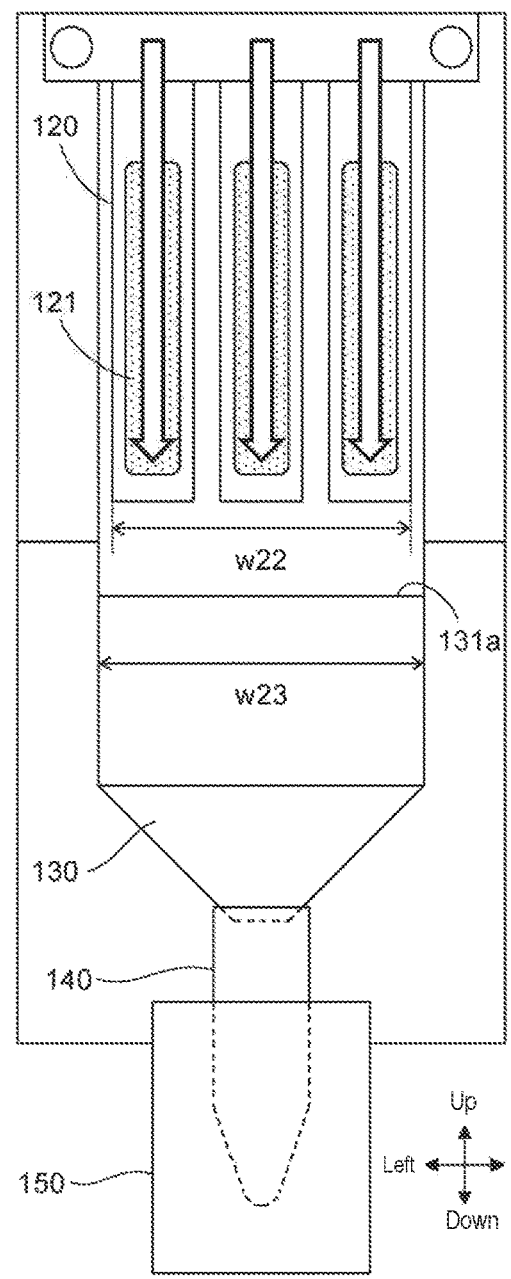

In the first embodiment, as shown in FIG. 4B, the width w1 of the blade 110 is wider than the width w2 of the slide 120, and one slide 120 is installed in the slide installation unit 51. However, as shown in FIG. 8A, the width w11 of the blade 110 may be narrower than the width w12 of the slide 120. As shown in FIG. 8B, a plurality of slides 120 also may be installed in the slide installation unit 51.

FIGS. 8A and 8B are front views schematically showing the structure in the vicinity of the slide installation unit 51 and the guide portion installation unit 52 according to the first modification.

In the structure shown in FIG. 8A, the width w11 of the blade 110 is narrower than the width w12 of the slide 120 and the width of the FFPE section 121 on the slide 120. In this case, as shown in FIG. 8A, the user performs the step of moving the blade 110 downward and scraping the FFPE section 121 a plurality of times by shifting the blade 110 in the left-right direction. The width w13 of the upper opening 131a of the guide portion 130 is set to be larger than the width w12 of the slide 120. In this way all the FFPE sections 121 scraped off by the blade 110 can be guided to the guide portion 130.

In the structure shown in FIG. 8B, the width w21 of the blade 110 is wider than the width of the slide 120, but a plurality of slides 120 are installed in the slide installation unit 51, and the width from the left end to the right end of the plurality of slides 120. w22 is wider than the width w21 of the blade 110. Also in this case, as shown in FIG. 8B, the user performs the step of moving the blade 110 downward and scraping the FFPE section 121 a plurality of times by shifting the blade 110 in the left-right direction. Since the width w23 of the upper opening 131a of the guide portion 130 is larger than the width w22 of the left and right ends of the plurality of slides 120, all the FFPE sections 121 scraped by the blade 110 can be guided to the guide portion 130.

Figure 9:
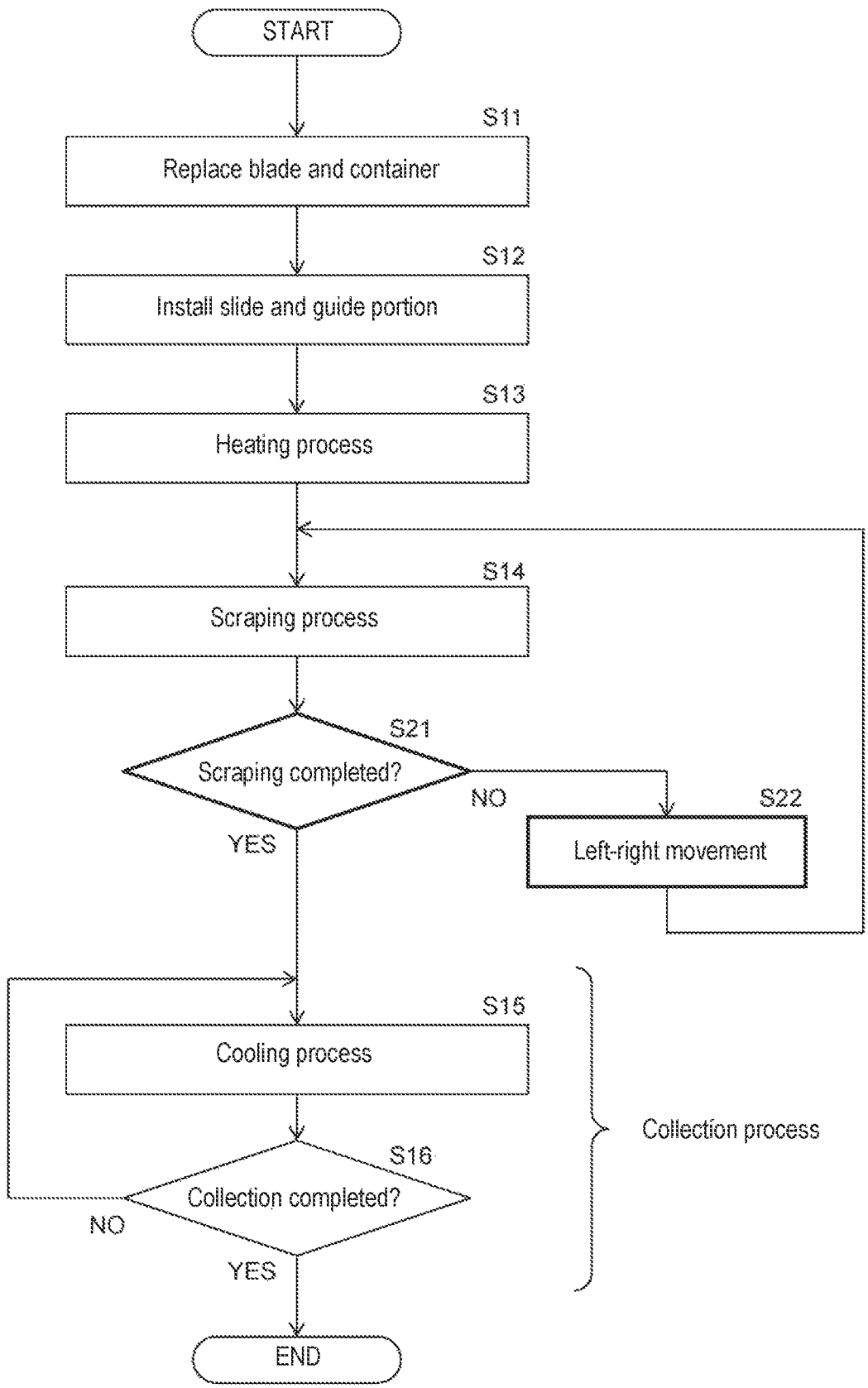
FIG. 9 is a flowchart showing a sample scraping method using a sample scraping device according to Modification 1.

FIG. 9 is a flowchart showing a sample scraping method using the sample scraping device 1 according to the modified example 1. FIG. 9 is a flowchart applied to both cases of FIGS. 8A and 8B.

In the first modification, steps S21 and S22 are added between steps S14 and S15 as compared with the flowchart of the first embodiment shown in FIG. 7. Hereinafter, the components different from those of the first embodiment will be described.

When the scraping process of step S14 is completed, the user determines whether all the scraping of the FFPE section 121 is completed. When the scraping is not completed (step S21: NO), the user moves the blade 110 in the left-right direction in step S22, and performs the scraping process of step S14 again. In this way, when all the necessary scraping of the FFPE section 121 is completed (step S21: YES), the user advances the process to steps S15 and S16 to perform the collection step.

In FIG. 9, the collection step is performed after all the scraping of the FFPE section 121 is completed, but alternatively, the collection step and the left-right movement step may be performed for each scraping step in step S14.

Effect of the First Modification

According to the first modification, the step of scraping the FFPE section 121 in step S14 is executed a plurality of times by shifting the blade 110 in the direction (left-right direction) intersecting the downward direction (shaving direction). In this way even when the width w12 of the slide 120 is wider than the width w11 of the blade 110 as shown in FIG. 8A, the FFPE section 121 can be evenly scraped from the slide 120 and collected. As shown in FIG. 8B, even when the width w22 of the left and right ends of the plurality of slides 120 is wider than the width w21 of the blade 110, the FFPE section 121 can be evenly scraped and collected from the plurality of slides 120.

Second Modification

In the second modification, the sample scraping device 1 further includes a vibrating unit 70 that vibrates the guiding portion 130 as compared with the first embodiment.

Figure 10:
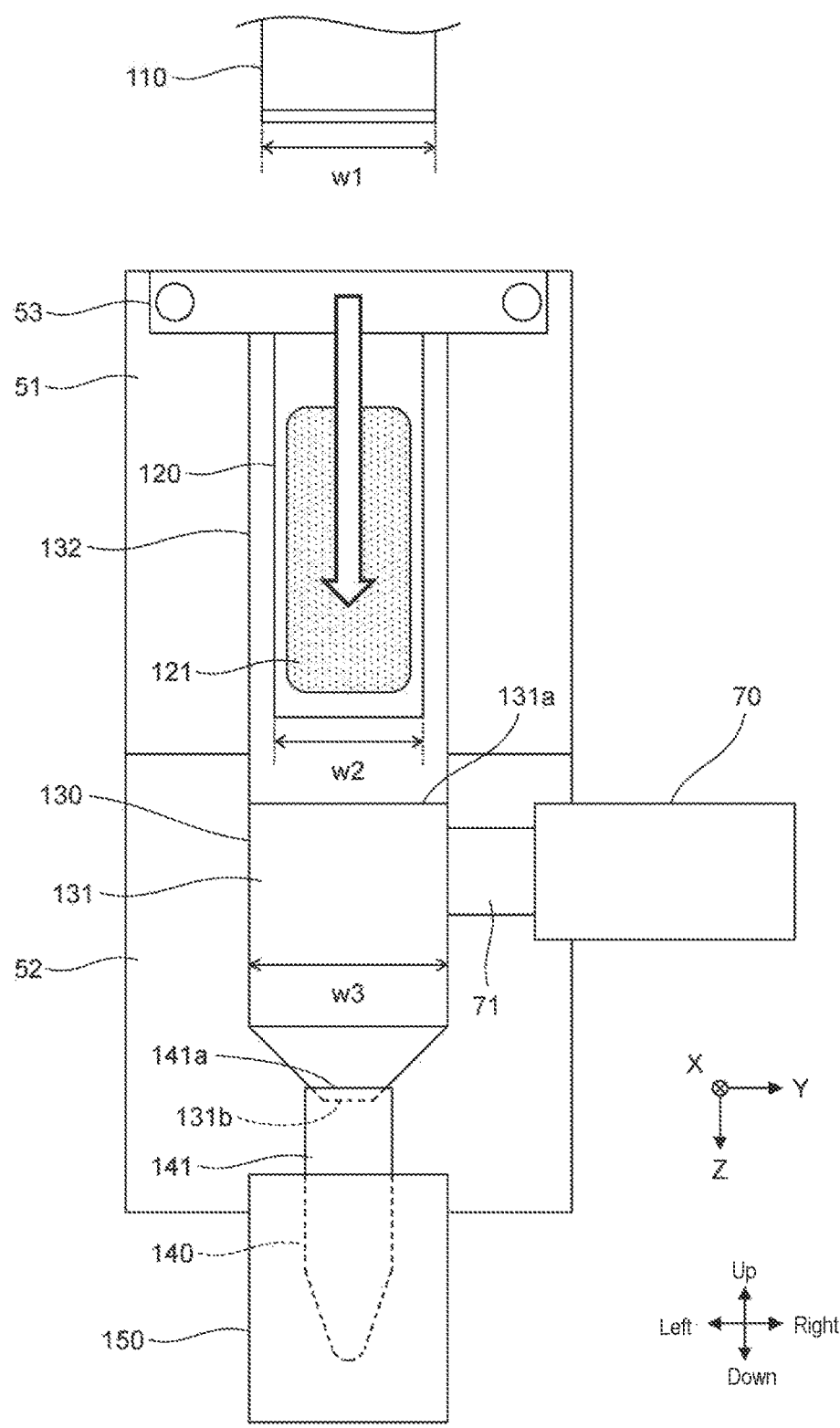
FIG. 10 is a front view schematically showing structures in the vicinity of a slide installation unit and a guide portion installation unit according to a second modification.

FIG. 10 is a front view schematically showing a structure in the vicinity of the slide installation unit 51 and the guide portion installation unit 52 according to the second modification.

The vibrating unit 70 includes a vibrator 71 and a mechanism for driving the vibrator 71. The vibrating unit 70 is installed in the housing 10 (see FIG. 1) so that the vibrator 71 comes into contact with the side surface of the guiding portion 130.

Figure 11:
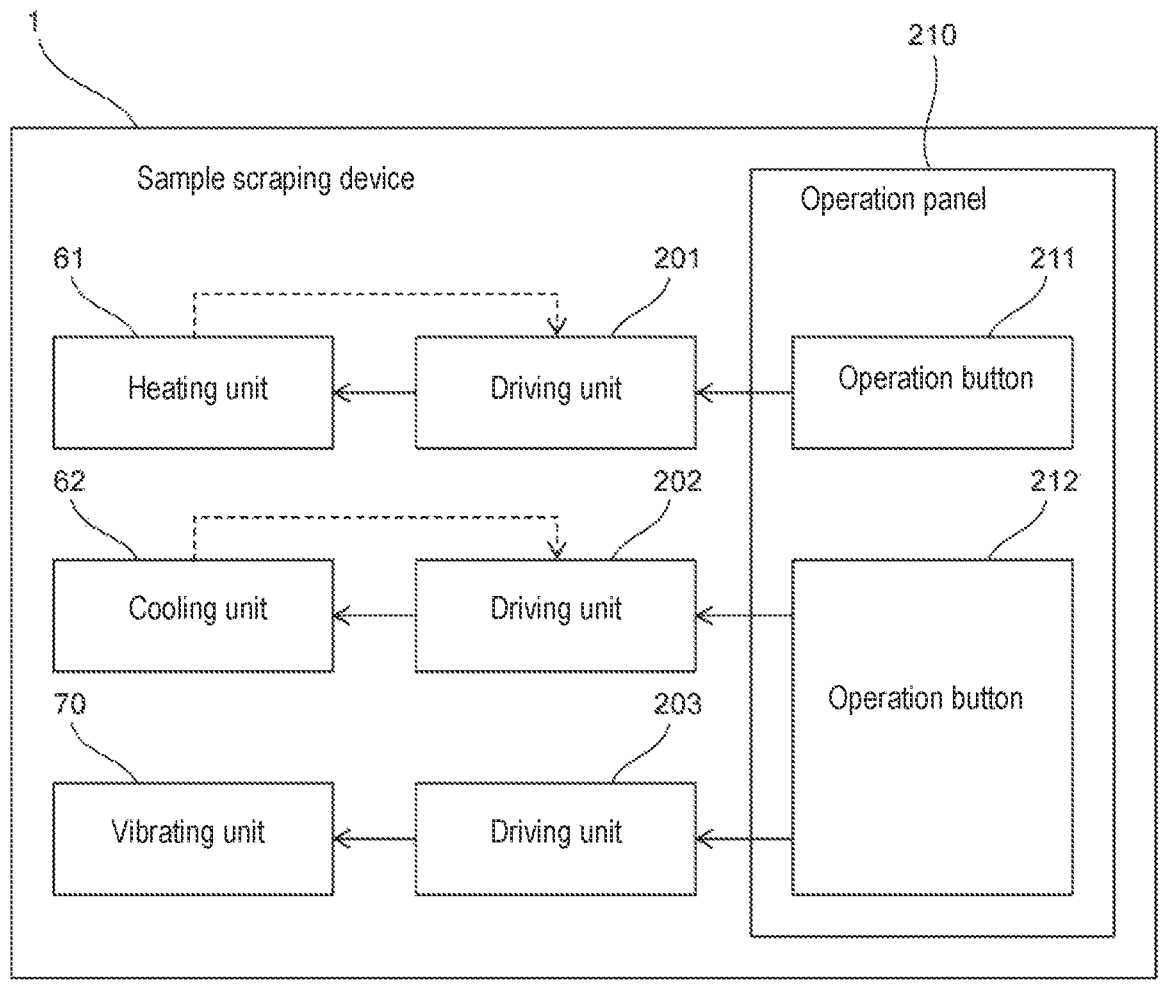
FIG. 11 is a block diagram showing a structure of a sample scraping device according to Modification 2.

FIG. 11 is a block diagram showing the structure of the sample scraping device 1 according to the second modification.

The sample scraping device 1 further includes a vibrating unit 70 and a driving unit 203, as compared with the structure of the first embodiment of FIG. 6. The operation button 212 is connected to the drive units 202 and 203, and when the user operates the operation button 212, the drive unit 202 drives the cooling unit 62 and the drive unit 203 drives the vibrating unit 70 in response to the operation. The drive unit 203 controls the vibrating unit 70 so that the vibrator 71 vibrates at a predetermined frequency.

Figure 12:
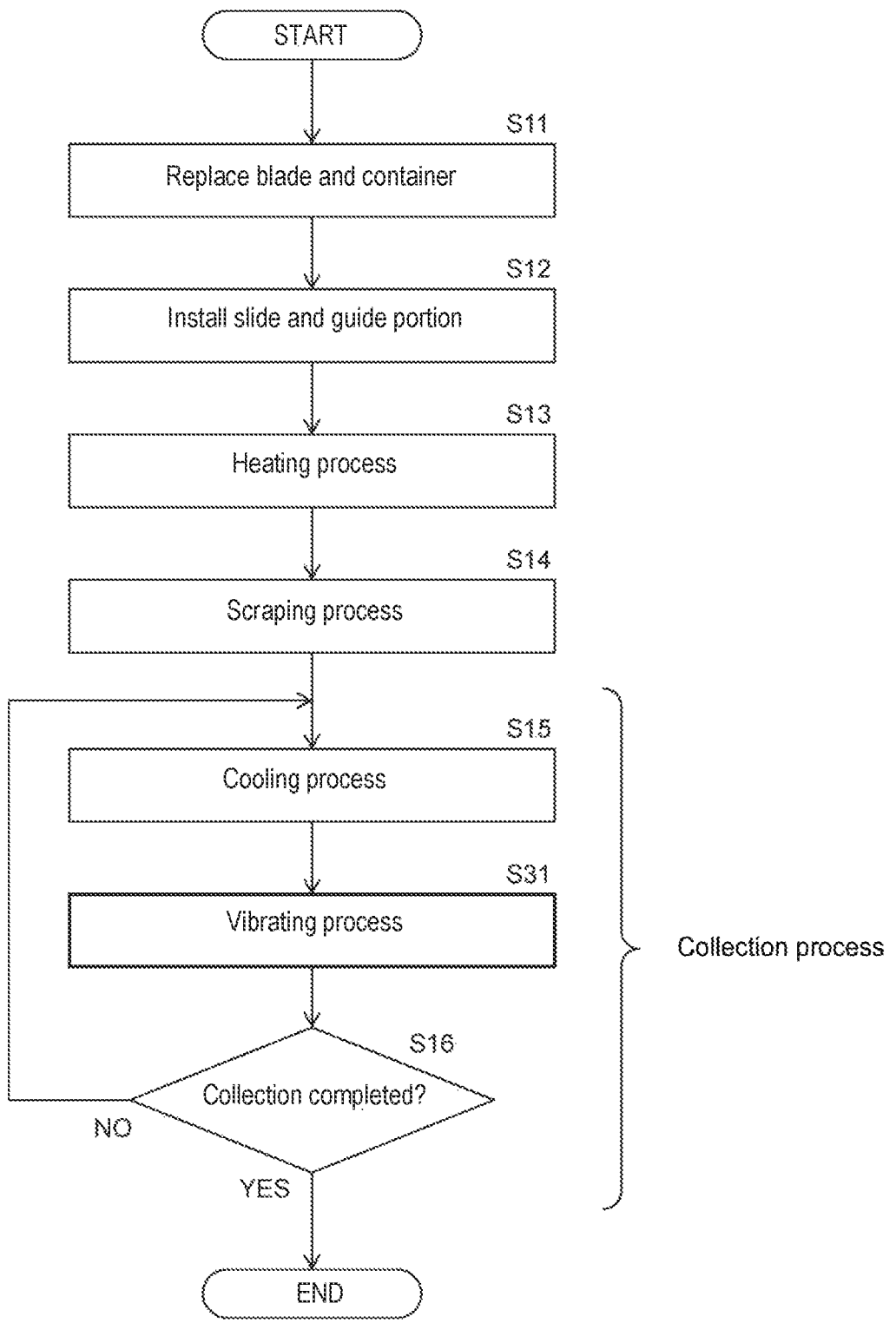
FIG. 12 is a flowchart showing a sample scraping method using a sample scraping device according to Modification 2.

FIG. 12 is a flowchart showing a sample scraping method using the sample scraping device 1 according to the second modification.

In the second modification, step S31 is added between steps S15 and S16 as compared with the flowchart of the first embodiment shown in FIG. 7. Hereinafter, the components different from those of the first embodiment will be described.

When the scraping process of step S14 is completed, the user executes the collecting step. The collecting step of the second modification is composed of a cooling process of step S15, a vibrating process of step S31, and a determination of step S16. The user executes steps S15 and S31 in parallel.

Specifically, in the cooling process of step S15, the user positions the blade 110 on the rear inner side surface 131c and operates the operation button 212 (see FIG. 11). In this way the scraped portion of the FFPE section 121 on the blade 110 is cooled (step S15), and the guide portion 130 is vibrated by driving the vibrating unit 70 (step S31). The user continues to execute steps S15 and S31 until the scraped portion of the FFPE section 121 on the blade 110 is collected in the container 140. When the scraped portion is collected (step S16: YES), the process of FIG. 12 is completed.

Effect of the Second Modification

In the second modification, as shown in FIG. 12, the collection step includes a vibration step of vibrating the guide unit 130. In this way the FFPE section 121 is less likely to stay in the guiding portion 130, so that the scraped portion of the FFPE section 121 can be more reliably guided to the container 140.

Third Modification

In the third modification, as compared with the first embodiment, the sample scraping device 1 further includes an ionizer 80 that sprays ions into the inside of the guide unit 130.

Figure 13:
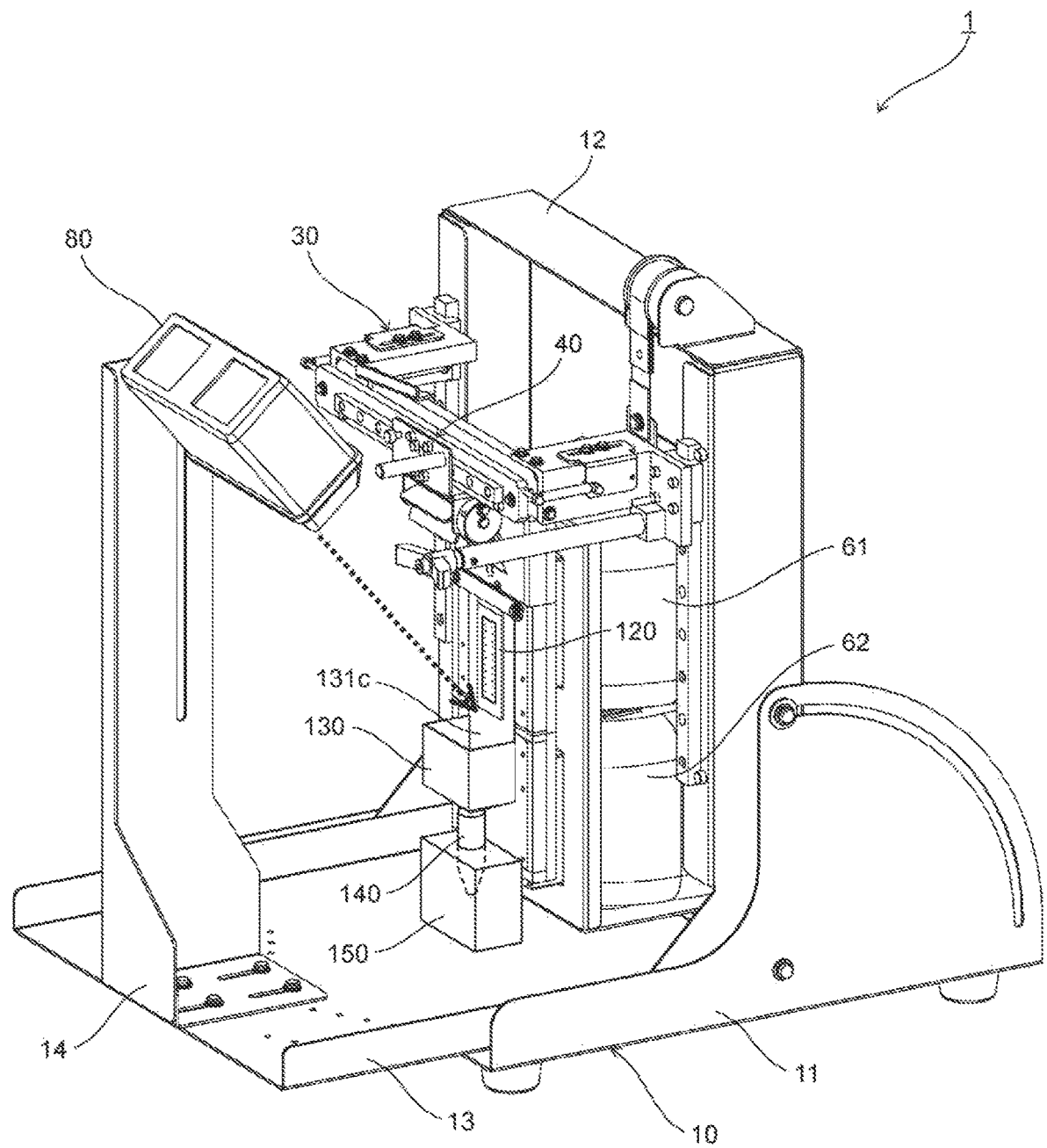
FIG. 13 is a perspective view showing a structure of a sample scraping device according to Modification 3.

FIG. 13 is a perspective view showing the structure of the sample scraping device 1 according to the third modification.

The ionizer 80 is installed on the support base 14 so that the direction in which the ions are sprayed faces the inside of the guide portion 130. The support base 14 is installed on the container mounting member 13 of the housing 10.

Figure 14:
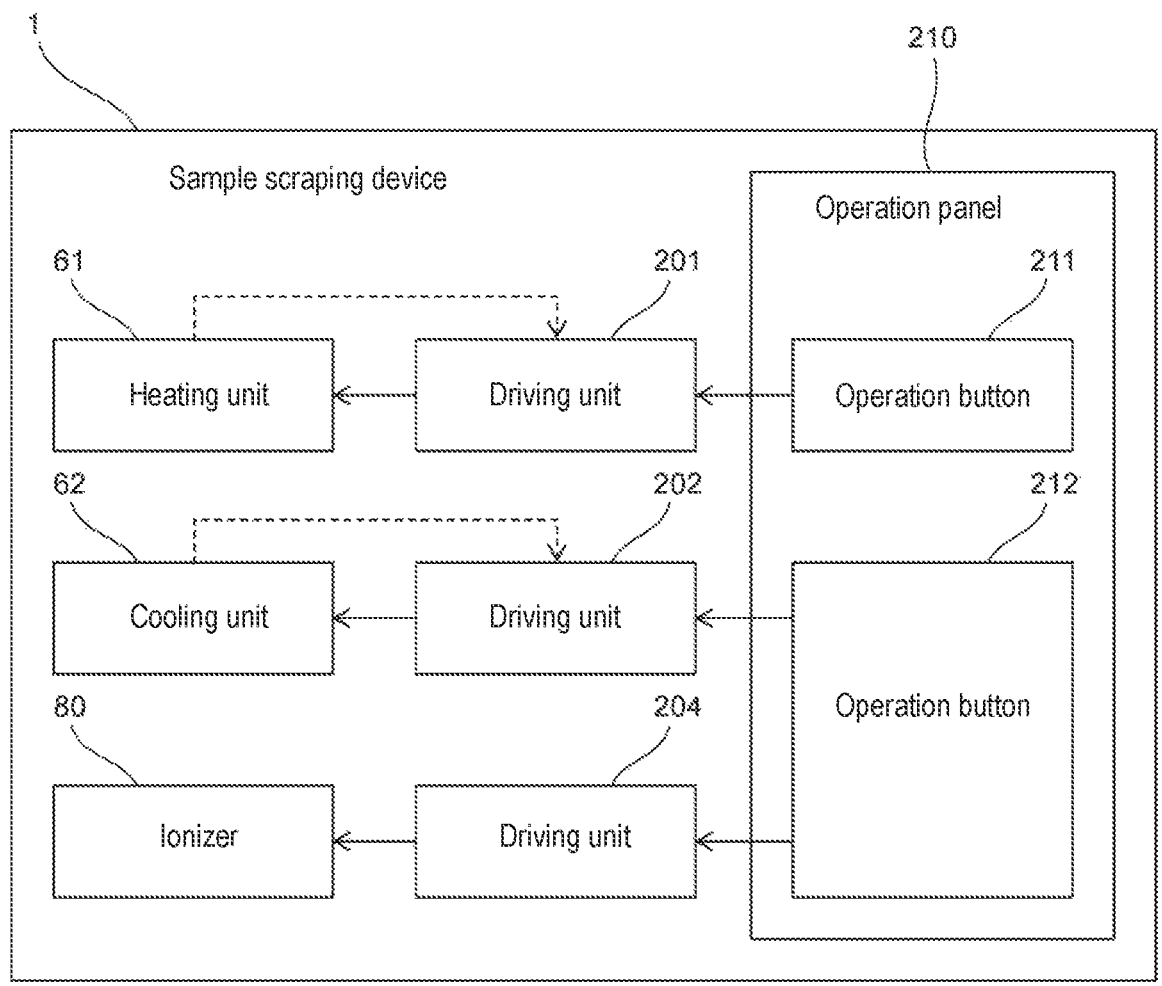
FIG. 14 is a block diagram showing a structure of a sample scraping device according to Modification 3.

FIG. 14 is a block diagram showing the structure of the sample scraping device 1 according to the third modification.

The sample scraping device 1 further includes an ionizer 80 and a driving unit 204 as compared with the structure of the first embodiment of FIG. 6. The operation button 212 is connected to the drive units 202 and 204, and when the user operates the operation button 212, the drive unit 202 drives the cooling unit 62 and the drive unit 204 drives the ionizer 80 in response to the operation. The drive unit 204 controls the ionizer 80 so that ions are sprayed from the ionizer 80 at a predetermined output.

Figure 15:
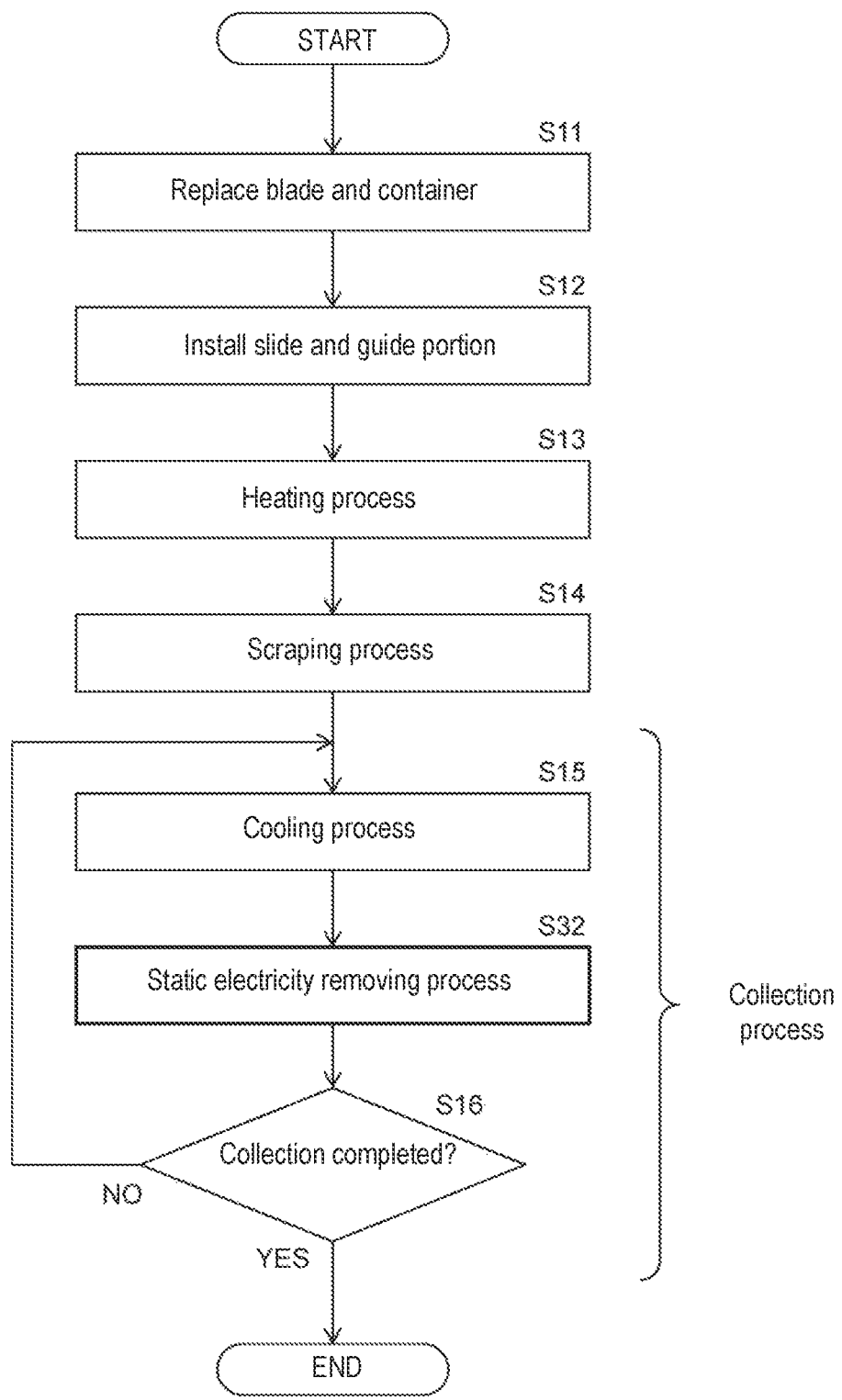
FIG. 15 is a flowchart showing a sample scraping method using a sample scraping device according to Modification 3.

FIG. 15 is a flowchart showing a sample scraping method using the sample scraping device 1 according to the third modification.

In the third modification, step S32 is added between steps S15 and S16 as compared with the flowchart of the first embodiment shown in FIG. 7. Hereinafter, the components different from those of the first embodiment will be described.

When the scraping process of step S14 is completed, the user executes the collecting step. The collecting step of the third modification is composed of a cooling process of step S15, a static electricity removing process of step S32, and a determination of step S16. The user executes steps S15 and S32 in parallel.

Specifically, in the cooling process of step S15, the user positions the blade 110 on the rear inner side surface 131c and operates the operation button 212 (see FIG. 11). In this way the scraped portion of the FFPE section 121 on the blade 110 is cooled (step S15), ions are sprayed into the guide portion 130 by driving the ionizer 80, and the scraped portion of the FFPE section 121 on the blade 110 is sprayed such that the static electricity on the inner surface of the guide portion 130 is removed (step S32). The user continues to execute steps S15 and S32 until the scraped portion of the FFPE section 121 on the blade 110 is collected in the container 140. When the scraped portion is recovered (step S16: YES), the process of FIG. 15 is completed.

Effect of the Third Modification

In the third modification 3, as shown in FIG. 15, the collecting step includes a static electricity removing step. In the static electricity removing step, ions are sprayed on the scraped portion of the FFPE section 121 remaining on the blade 110. In this way the static electricity of the scraped portion remaining on the blade 110 is removed, so that the scraped portion can be dropped from the blade 110 and smoothly guided to the container 140. Further, in the static electricity removing step, ions are sprayed on the guide portion 130. In this way static electricity on the inner surface of the guide portion 130 is removed, so that the scraped portion dropped from the blade 110 can be suppressed from staying at the guide portion 130, and the scraped portion can be smoothly guided to the container 140.

Second Embodiment

In the first embodiment, the user operates the vertical movement lever 32 to move the blade 110 in the vertical direction, and operates the left-right movement lever 42 to move the blade 110 in the horizontal direction. The user operates the switching lever 37 to switch between a state in which the blade 110 is forced backward by the spring 35 and a state in which the force is released. The user operates the operation buttons 211 and 212 to drive the heating unit 61, the cooling unit 62, the vibration unit 70, and the ionizer 80. On the other hand, in the second embodiment, these user operations are automatically performed.

Figure 16B:
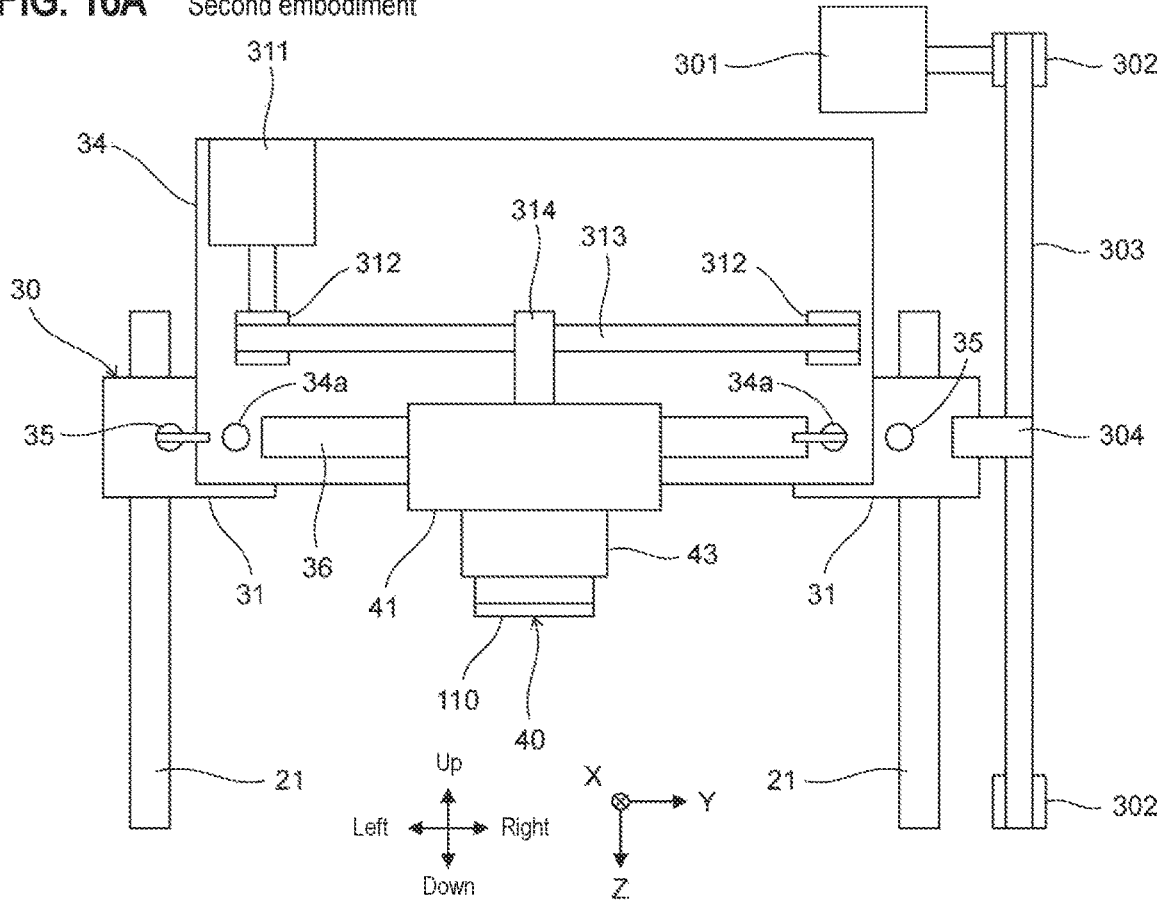
FIG. 16B is a plan view schematically showing the structure of the sample scraping device according to the second embodiment.
Figure 16B:
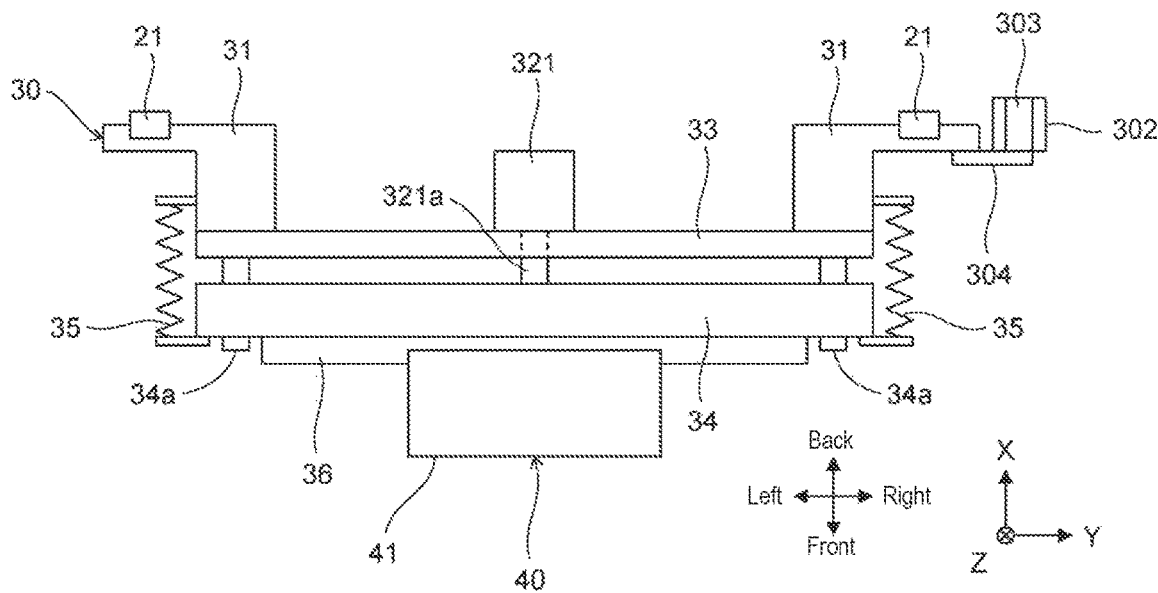

FIG. 16A is a front view schematically showing the structure of the sample scraping device 1 according to the second embodiment. FIG. 16B is a plan view schematically showing the structure of the sample scraping device 1 according to the second embodiment. In FIGS. 16A and 16B, the vicinity of the vertical moving unit 30 and the horizontal moving unit 40 is shown for convenience.

As shown in FIGS. 16A and 16B, the sample scraping device 1 has a motor 301, a pair of pulleys 302, a belt 303, and a support member 304, a motor 311 and a pair of pulleys 312, a belt 313, a support member 314, and a motor 321 as compared with the structure of the first embodiment of FIG. 1. The motors 301, 311 and 321 are composed of a stepping motor. As compared with the structure of the first embodiment of FIG. 1, the pulley 22, the belt 23, the vertical movement lever 32, the switching lever 37, and the left-right movement lever 42 are omitted.

Note that FIG. 16B omits the motor 311, the pair of pulleys 312, the belt 313, and the support member 314 for convenience.

The motor 301 and the pair of pulleys 302 are installed on the wall member 12 of the housing 10. The rotation shaft of the motor 301 is connected to one pulley 302, and the belt 303 is hung on a pair of pulleys 302. The support member 304 connects the belt 303 and the vertical movement member 31 on the right side. When the motor 301 is driven, the support member 304 moves in the vertical direction along the belt 303, and the vertical movement unit 30 connected to the support member 304 moves in the vertical direction.

The motor 311 and the pair of pulleys 312 are installed on the front-rear moving member 34. The rotation shaft of the motor 311 is connected to one pulley 312, and the belt 313 is reeved on a pair of pulleys 312. The support member 314 connects the belt 313 and the left-right moving member 41. When the motor 311 is driven, the support member 314 moves in the left-right direction along the belt 313, and the left-right moving unit 40 connected to the support member 314 moves in the left-right direction.

The motor 321 is installed in the plate member 33, and the rotation shaft 321a of the motor 321 extends forward to the front-rear moving member 34 through a hole provided in the plate member 33. When the motor 321 is driven, the tip of the rotating shaft 321a moves in the front-rear direction. In this way the front-rear moving member 34 forced to approach the plate member 33 by the pair of springs 35 moves back and forth while being pushed forward by the rotating shaft 321a.

Figure 17:
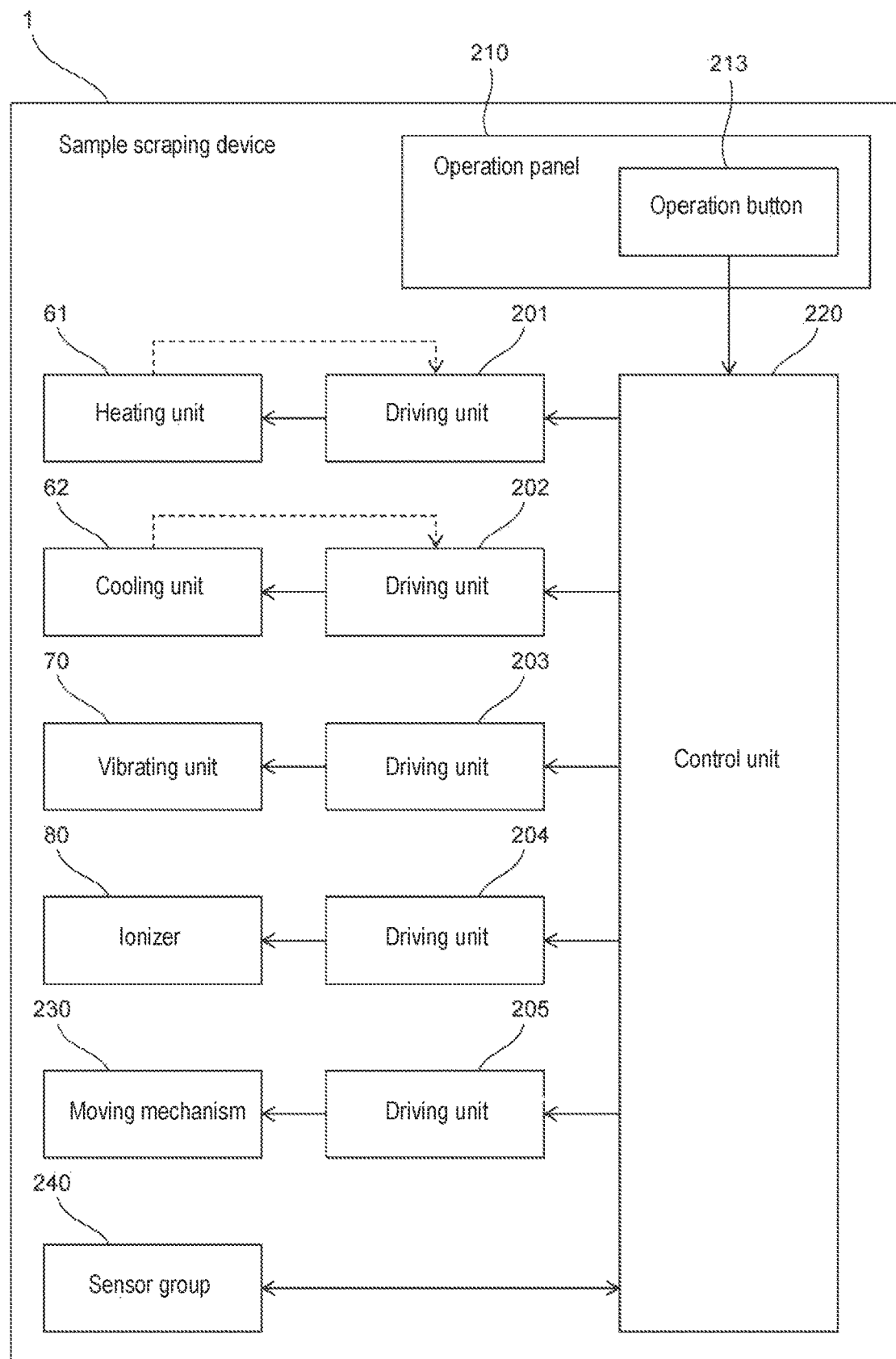
FIG. 17 is a block diagram showing a structure of a sample scraping device according to a second embodiment.

FIG. 17 is a block diagram showing the structure of the sample scraping device 1 according to the second embodiment.

Compared with the structure of the first embodiment of FIG. 6, the sample scraping device 1 has the vibrating unit 70 and the driving unit 203 of the first modification shown in FIG. 11 and the ionizer 80 of the second modification shown in FIG. 14A, and the driving unit 204, a moving mechanism 230, a drive unit 205, a control unit 220, and a sensor group 240.

The moving mechanism 230 includes a structure in which the blade 110 is moved relative to the slide 120. Specifically, the moving mechanism 230 includes a guide rail 21, a pulley 22, a belt 23, a vertical moving unit 30, a left-right moving unit 40 and, as shown in FIGS. 16A and 16B, a pair of pulleys 302, a belt 303, a support member 304, a pair of pulleys 312, a belt 313, and a support member 314. The drive unit 205 includes the motors 301, 311 and 321 shown in FIGS. 16A and 16B, and the drive unit 205 drives the moving mechanism 230. The sensor group 240 includes a plurality of sensors for detecting the position of the blade 110. Each sensor of the sensor group 240 is composed of, for example, a reflection type optical sensor or a transmission type optical sensor.

The control unit 220 is composed of, for example, a CPU and a memory. The control unit 220 controls the drive units 201 to 205 based on the detection signals of the sensors of the sensor group 240, and drives the heating unit 61, the cooling unit 62, the vibrating unit 70, the ionizer 80, and the moving mechanism 230, respectively.

The operation panel 210 includes an operation button 213 for starting the operation of the sample scraping device 1. When the user operates the operation button 213, the control unit 220 detects the position of the blade 110 based on the detection signal of each sensor of the sensor group 240, and sequentially performs the processing performed by the user in the first embodiment.

Figure 18:
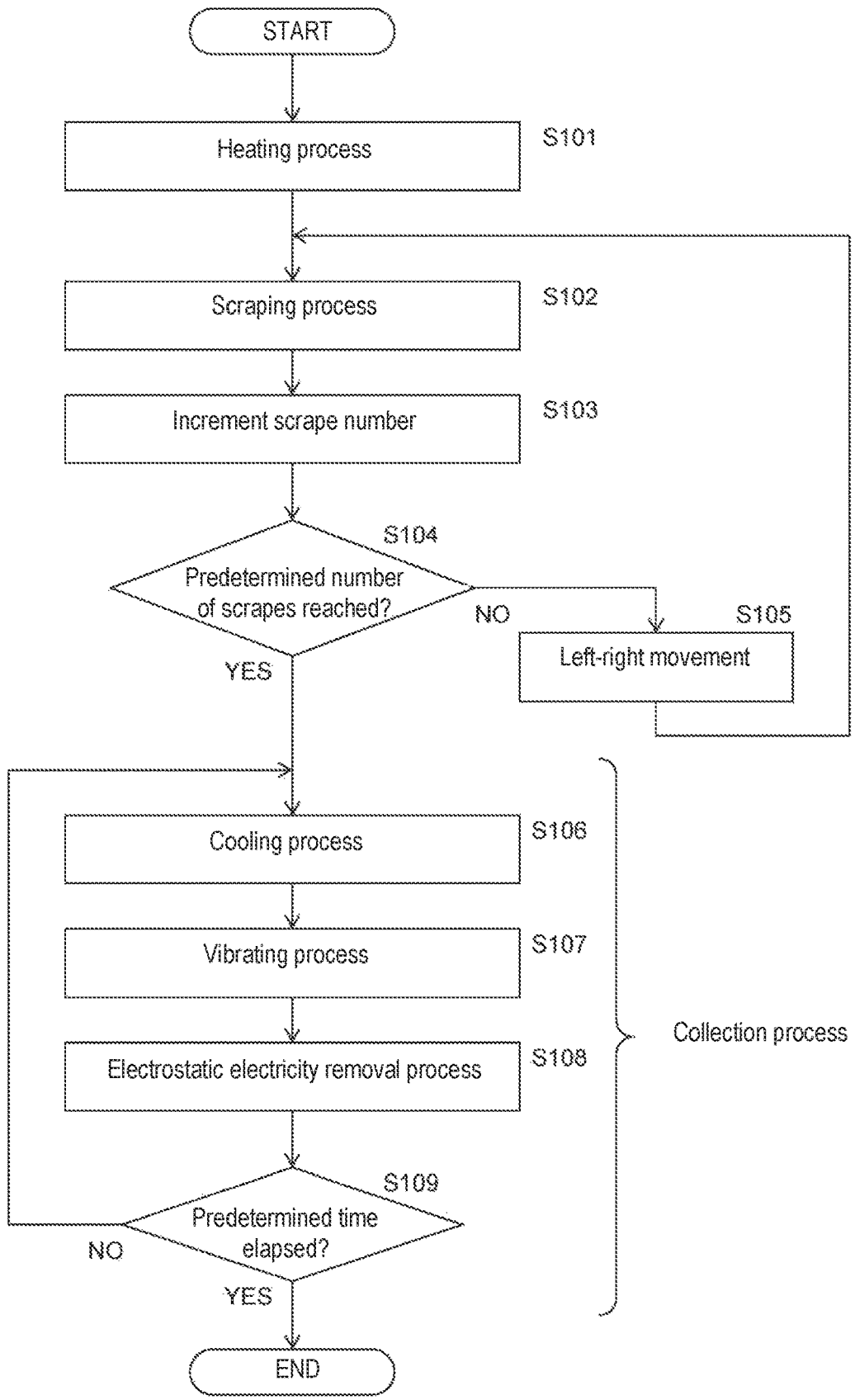
FIG. 18 is a flowchart showing a process of a sample scraping device according to a second embodiment.

FIG. 18 is a flowchart showing the processing of the sample scraping device 1 according to the second embodiment.

Prior to the processing by the sample scraping device 1, the user replaces the blade 110 and the container 140, and installs the slide 120 and the guide portion 130, as in steps S11 and S12 of the first embodiment of FIG. 7. Then, the user operates the operation button 213 (see FIG. 17) to start the processing of the sample scraping device 1.

In the heating process of step S101, the control unit 220 drives the heating unit 61 by controlling the drive unit 201 to heat the FFPE section 121 on the slide 120 installed in the slide installation unit 51, as in FIG. 3A. In the scraping process of step S102, the control unit 220 drives the moving mechanism 230 (see FIG. 17) by controlling the driving unit 205, and moves the blade 110 to scrap the FFPE section 121 on the slide 120 as in FIG. 3B. In the incrementing process of step S103, the control unit 220 increases the number of scrapes by one.

In step S104, the control unit 220 determines whether the number of executions (number of scrapes) of step S102 has reached a predetermined number of times. When the number of scrapings has not reached the predetermined number (step S104: NO), the control unit 220 drives the movement mechanism 230 to shift the blade 110 to the right or left by a predetermined movement distance by controlling the drive unit 205, and executes steps S102 and S103 again. The predetermined number of times and the predetermined movement distance are stored in advance in the memory of the control unit 220 according to the width of the blade 110 and the width of the slide 120. Note that when the width of the blade 110 is larger than the width of the slide 120, the scraping step is performed only once, such that the processes of steps S103 to 105 can be omitted.

When the number of scrapes reaches a predetermined number (step S104: YES), the control unit 220 executes the collection step. The collection step is composed of a cooling process of step S106, a vibrating process of step S107, a static electricity removing process of step S108, and a determination process of step S109.

In the cooling process of step S106, the control unit 220 controls the drive unit 205 to drive the moving mechanism 230 to position the tip of the blade 110 on the rear inner side surface 131c as in FIG. 5A; and control the drive unit 202 to drive the cooling unit 62 to cool the scraped portion of the FFPE section 121 on the blade 110. The control unit 220 drives the vibrating unit 70 to vibrate the guide portion 130 by controlling the drive unit 203 in step S107 in parallel with the cooling process of step S106, and in step S108 controls the drive unit 204 to drive the ionizer 80 to blow ions into the guide portion 130.

In step S109, the control unit 220 determines whether a predetermined time has elapsed since the collection process was started. The predetermined time is stored in the memory of the control unit 220 in advance. If the predetermined time has not elapsed (step S109: NO), the control unit 220 continues the processing of steps S106 to S108. On the other hand, when the predetermined time has elapsed (step S109: YES), the processing of the sample scraping device 1 is completed.

Effect of the Second Embodiment

According to the second embodiment, the same effects as those of the first embodiment and the first to third modifications are achieved.

Since the blade 110 is moved by the moving mechanism 230, the user does not need to operate the vertical movement lever 32 to move the blade 110 up and down, and the user does not need to operate the left-right movement lever 42 to move the blade 110 left and right. Hence, the burden on the user can be reduced and the FFPE section 121 can be smoothly collected.

Third Embodiment

When the sample scraping device 1 can be automatically operated as shown in the second embodiment, the case may be arranged so as to surround the sample scraping device 1 so that the interior of the case may be dehumidified as shown below.

FIG. 19A is a perspective view schematically showing the structure of the third embodiment.

In the third embodiment, the case 410 is arranged so as to circumscribe the periphery of the sample scraping device 1, and the dehumidifier 401 is arranged inside the case 410. The operation panel 210 is arranged outside the case 410 and is connected to the sample scraping device 1 and the dehumidifier 401.

In the third embodiment, the user 400 works from the outside of the case 410. The user 400 moves the door 411 provided in the case 410 upward to open the inside of the case 410. In this state, the user 400 replaces the blade 110, the slide 120, the guide portion 130, and the container 140. When the replacement is completed, the user 400 closes the door 411 and seals the inside of the case 410. Then, the user 400 operates the button of the operation panel 210 to drive the dehumidifier 401 and start the operation of the sample scraping device 1.

Instead of dehumidifying using the case 410, the inside of the room in which the sample scraping device 1 is installed may be dehumidified as shown below.

FIG. 19B is a perspective view schematically showing the structure in this case.

In this modification, the sample scraping device 1 is arranged inside the room 420, and the dehumidifier 401 is arranged inside the room 420. The operation panel 210 is arranged inside the room 420 and is connected to the sample scraping device 1 and the dehumidifier 401.

In this modification, the user 400 works inside room 420. The user 400 enters the room 420 through the door 421 and closes the door 421 to seal the inside of the room 420. Then, the user replaces the blade 110, the slide 120, the guide portion 130, and the container 140. When the replacement is completed, the user 400 operates the button on the operation panel 210 to drive the dehumidifier 401 and start the operation of the sample scraping device 1. Note that the sample scraping device 1 in this case may be any of the sample scraping devices 1 and 2 and the modified examples 1 to 3.

Effect of the Third Embodiment

According to the third embodiment, the same effects as those of the first and second embodiments and the first to third modifications are obtained.

Since the humidity inside the case 410 and the room 420 is lowered by driving the dehumidifier 401, the occurrence of condensation on the FFPE section 121 is suppressed when the scraped portion of the FFPE section 121 on the blade 110 is cooled. In this way the scraped portion on the blade 110 can be smoothly guided to the container 140.

Other Modifications

In the heating step of the first to third embodiments and the first to third modifications as shown in FIG. 3A, the heating unit 61 heats the slide installation unit 51 to indirectly heat the FFPE section 121 disposed on slide installation unit 51. However, alternatively, a heater or an infrared lamp also may be provided in front of the slide installation portion 51, and warm air may be blown to directly heat the FFPE section 121 on the slide 120.

In the cooling step, as shown in FIG. 5A, the cooling unit 62 cools the guide portion installation unit 52, so that the scraped portion of the FFPE section 121 on the blade 110 arranged in contact with the rear inner side surface 131c was indirectly cooled. However, alternatively, a cooling device also may be provided in front of the guide portion installation unit 52, and the scraped portion of the FFPE section 121 on the blade 110 may be directly cooled by blowing cold air.

In the heating step, both the heating of the slide installation unit 51 and the blowing of warm air may be performed. In the cooling step, both the cooling of the guide portion installation unit 52 and the blowing of cold air may be performed.

However, when warm air is blown, the FFPE section 121 on the slide 120 may be scattered by the hot air, and when cold air is blown, the scraped portion of the FFPE section 121 on the blade 110 is also may be scattered by the cold air. Therefore, as in the above first through third embodiments and the first through third modifications 1 through 3, it is preferable that the heating is performed only through the slide installation unit 51, and the cooling is performed only through the guide portion installation unit 52.

In the first to third embodiments and the first to third modifications, the heating unit 61 includes a Peltier element for heating the slide installation unit 51, but a heater may be provided instead.

In the cooling process of the first to third embodiments and the first to third modifications, the tip of the blade 110 comes into contact with the rear inner side surface 131c (cooling surface) of the guide portion 130 as shown in FIG. 5A, such that the scraped portion of the FFPE section 121 on the blade 110 was cooled. However, the invention is not limited to this configuration insofar as, the blade 110 does not have to be in contact with the rear inner side surface 131c, and a gap may be provided between blade 110 and the 131c if the blade 110 is thermally coupled to the rear inner side surface 131c such that the blade 110 and the rear inner surface are not in contact with each other.

In the first to third embodiments and the first to third modifications, as shown in FIG. 1, the wall member 12 is arranged perpendicular to the horizontal plane, so that the slide installation unit 51 and the guide portion installation unit 52 are arranged perpendicular to the horizontal plane. However, the present invention is not limited to this, and in FIG. 1, the wall member 12 may be arranged at an angle from the perpendicular plane to the horizontal plane. In this case, the slide installation unit 51 and the guide portion installation unit 52 are also tilted from a state perpendicular to the horizontal plane. However, in order to smoothly collect the FFPE section 121 scraped from the slide 120 into the container 140, it is preferable that the wall member 12 is arranged so as to be perpendicular to the horizontal plane as shown in FIG. 1.

In the first to third embodiments and the first to third modifications, the slide 120 is installed in the slide installation unit 51, and the blade 110 is forced backward by the force exerted by the spring 35. However, the present invention is not limited to this, and the spring 35 on the blade 110 side may be omitted, and a spring for forcing the slide installation unit 51 in the direction closer to the blade 110 may be provided on the slide installation unit 51 side. Springs may be provided on both the blade 110 side and the slide installation unit 51 side to exert force on the blade 110 and the slide installation unit 51 to come close to each other.

In the first to third embodiments and the first to third modification, the slide 120 is installed in the slide installation unit 51, and the blade 110 is moved so that the blade 110 is moved relative to the slide 120. However, the present invention is not limited to this, inasmuch as the blade 110 may be moved relative to the slide 120 by installing the blade 110 on the wall member 12 and moving the slide installation unit 51. The blade 110 may be moved relative to the slide 120 by moving both the blade 110 and the slide 120.

In the first to third embodiments and the first to third modifications, the guide portion 130 is made of resin, but also may be made of SUS or aluminum. In this case, since the thermal conductivity of the guide portion 130 is higher than that of the resin, the blade 110 in contact with the rear inner side surface 131c can be smoothly cooled. In this case, it is preferable to perform treatments such as sterility and cleaning of the guide portion 130 according to the replacement of the slide 120.

In the first to third embodiments and the first to third modifications, the connecting surface 132 is installed in the slide installation unit 51, so that the guide portion 130 is installed in the guide portion installation unit 52. However, the present invention is not limited to this, inasmuch as the guide portion 130 also may be installed in the guide portion installation unit 52 by installing the connection surface 132 having a length in the vertical direction shorter than that in the example of FIG. 2 in the guide portion installation unit 52. In this case, the slide 120 is installed in the slide installation unit 51 so that the rear surface is in contact with the front surface of the slide installation unit 51. It is preferable that the connection surface 132 of the guide portion 130 to be replaced for each slide 120 is arranged between the slide 120 and the slide installation unit 51 so that the FFPE section 121 scraped from the slide 120 is prevented from causing contamination via the slide installation unit 51.

In the second embodiment, although each sensor of the sensor group 240 was used to detect the position of the blade 110; alternatively, the position of the blade 110 may be detected based on a still image or a moving image taken by a camera. The position of the blade 110 also may be detected based on the number of steps of the motors 301, 311 and 321 of the moving mechanism 230.

In the second embodiment, the cooling process of step S106, the vibrating process of step S107, and the static electricity removing process of step S108 need not be started in this order. Steps S106 to S108 may be started in any order.

In the second embodiment, when the predetermined time elapses in step S109, it is determined that the collection of the scraped portion of the FFPE section 121 is completed; however, whether the scraped portion is recovered may also be determined based on an optical sensor, camera or the like. When an optical sensor is used, the control unit 220 determines the presence or absence of a scraped portion in the container 140 based on the detection signal of the optical sensor. When a camera is used, the control unit 220 determines whether there is a scraped portion in the container 140 based on a still image or a moving image of the container 140 taken by the camera.

In the second embodiment, although the moving mechanism 230 and the driving unit 205 are shown as a configuration for moving the blade 110, the configuration for moving the blade 110 is not limited to this. In the second embodiment, the blade 110, the slide 120, the guide portion 130, and the container 140 are replaced by the user, but these exchanges may be automatically performed by the mechanism unit.

As shown in FIG. 19A, when the periphery of the sample scraping device 1 is sealed by the case 410, the FFPE section 121 on the slide 120 may be heated by controlling the temperature inside the case 410 instead of using the heating unit 61. The scraped portion of the FFPE section 121 on the blade 110 may be cooled by controlling the temperature inside the case 410 instead of using the cooling unit 62. Similarly, as shown in FIG. 19B, when the periphery of the sample scraping device 1 is sealed by the room 420, the FFPE section 121 on the slide 120 may be heated by controlling the temperature in the room 420 instead of using the heating unit 61. The scraped portion of the FFPE section 121 on the blade 110 also may be cooled by controlling the temperature in the room 420 instead of using the cooling unit 62.

In the first to third embodiments and the first to third modifications, the biological tissue section held on the slide 120 is an FFPE section 121, but the present invention is not limited to this. For example, the biological tissue section also may be a frozen tissue section.

The embodiments of the present invention can be appropriately modified in various ways within the scope of the technical concepts described in the claims.

What is claimed is:

1. A sample scraping method for scraping and collecting a biological tissue section held on a slide, the method comprising:
   heating the biological tissue section held on the slide;
   scraping off the heated biological tissue section with a blade; and
   collecting the biological tissue section remaining on the blade into a container, wherein
   the collecting comprises cooling the biological tissue section remaining on the blade.

2. The sample scraping method according to claim 1, wherein
   the blade is thermally coupled to a cooling surface to cool the biological tissue section remaining on the blade.

3. The sample scraping method according to claim 1, wherein
cooling temperature of the biological tissue section remaining on the blade is 5° C. to 20° C.

4. The sample scraping method according to claim 1, wherein
in the scraping off the biological tissue section, the blade is elastically pressed against the biological tissue section.

5. The sample scraping method according to claim 1, wherein
the scraping off the biological tissue section is performed a plurality of times by shifting the blade in a direction intersecting the scraping direction.

6. The sample scraping method according to claim 1, wherein
in the scraping off the biological tissue section, an angle between a blade surface of the blade and a slide surface is 38° to 51°.

7. The sample scraping method according to claim 1, wherein
the heating the biological tissue section comprises heating an installation member on which the slide is installed.

8. The sample scraping method according claim 1, wherein
in the heating the biological tissue section, heating temperature of the biological tissue section is 40° C. to 50° C.

9. The sample scraping method according to claim 1, wherein
in the collecting the biological tissue section remaining on the blade, the biological tissue section dropped from the blade is guided to the container by a guide portion.

10. The sample scraping method according to claim 9, wherein
the guide portion has a funnel shape; and
width of an upper opening of the guide portion is larger than width of the biological tissue section held on the slide, and a lower opening of the guide portion is smaller than an opening of the container.

11. The sample scraping method according to claim 9, wherein
the collecting the biological tissue section remaining on the blade comprises vibrating the guide portion.

12. The sample scraping method according to claim 9, wherein
the collecting the biological tissue section remaining on the blade comprises spraying ions on the guide portion.

13. The sample scraping method according to claim 1, wherein
the blade is replaced every time the biological tissue section is replaced.

14. The sample scraping method according to claim 1, wherein
the biological tissue section is an FFPE section.

15. A sample scraping device for scraping and collecting a biological tissue section held on a slide, the device comprising:
a slide installation unit on which the slide holding the biological tissue section is installed;
a heating unit for heating the biological tissue section on the slide installed on the slide installation unit; and
a moving mechanism for scraping off the biological tissue section with a blade.

16. The sample scraping device according to claim 15, further comprising:
a cooling unit for cooling the biological tissue section remaining on the blade.

17. The sample scraping device according to claim 16, wherein
the cooling unit thermally binds the blade to a cooling surface to cool the biological tissue section remaining on the blade.

18. The sample scraping device according to claim 15, further comprising:
a press unit that elastically presses the blade against the biological tissue section.

19. The sample scraping device according to claim 15, further comprising:
a driving unit for driving the moving mechanism; and
a control unit for controlling the drive unit.

20. The sample scraping device according to claim 19, wherein
the control unit controls the driving unit so that the scraping off the biological tissue section is executed a plurality of times by shifting the blade in a direction intersecting a scraping direction.

21. The sample scraping device according to claim 15, wherein
the heating unit heats the biological tissue section on the slide installed on the slide installation unit by heating the slide installation unit.

22. The sample scraping device according to claim 15, further comprising:
a guide portion for guiding the biological tissue section dropped from the blade to a collection container arranged below the slide installation unit.

23. The sample scraping device according to claim 22, wherein
the guide portion has a funnel shape; and
width of an upper opening of the guide portion is larger than width of the biological tissue section held on the slide, and a lower opening of the guide portion is smaller than an opening of the collection container.

24. The sample scraping device according to claim 22, further comprising
a vibrating unit for vibrating the guide portion.

25. The sample scraping device according to claim 22, further comprising:
an ionizer for spraying ions on the guide portion.

26. A sample scraping method for scraping and collecting a biological tissue section held on a slide, the method comprising:
heating the biological tissue section held on the slide;
scraping off the heated biological tissue section with a blade; and
collecting the biological tissue section remaining on the blade into a container, wherein
in the heating the biological tissue section, heating temperature of the biological tissue section is 40° C. to 50° C.

* * * * *